(12) United States Patent
Riegel et al.

(10) Patent No.: US 7,759,422 B2
(45) Date of Patent: Jul. 20, 2010

(54) FINE-GRAINED WATER-ABSORBENT PARTICLES WITH A HIGH FLUID TRANSPORT AND ABSORPTION CAPACITY

(75) Inventors: Ulrich Riegel, Landstuhl (DE); Thomas Daniel, Waldsee (DE); Dieter Hermeling, Böhl-Iggelheim (DE); Mark Elliott, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 736 days.

(21) Appl. No.: 11/665,883

(22) PCT Filed: Oct. 14, 2005

(86) PCT No.: PCT/EP2005/011073
§ 371 (c)(1),
(2), (4) Date: Apr. 18, 2007

(87) PCT Pub. No.: WO2006/042704
PCT Pub. Date: Apr. 27, 2006

(65) Prior Publication Data
US 2008/0125533 A1    May 29, 2008

(30) Foreign Application Priority Data
Oct. 20, 2004   (DE) ................ 10 2004 051 242

(51) Int. Cl.
*C08G 63/60*   (2006.01)
(52) U.S. Cl. .............. 524/599; 525/329.9; 526/64
(58) Field of Classification Search ............ 526/64; 524/599; 525/329.9
See application file for complete search history.

(56) References Cited
U.S. PATENT DOCUMENTS

| | | | |
|---|---|---|---|
| 5,599,335 A | 2/1997 | Goldman et al. | |
| 6,766,817 B2 | 7/2004 | da Silva et al. | |
| 6,918,404 B2 | 7/2005 | Dias da Silva et al. | |
| 7,066,586 B2 | 6/2006 | da Silva et al. | |
| 2004/0077796 A1 | 4/2004 | Daniel et al. | |
| 2005/0245684 A1 | 11/2005 | Daniel et al. | |
| 2006/0036043 A1 | 2/2006 | Nestler et al. | |

FOREIGN PATENT DOCUMENTS

| | | |
|---|---|---|
| WO | WO-02/060983 | 8/2002 |
| WO | WO-2004/024816 | 3/2004 |
| WO | WO-2004/052949 | 6/2004 |
| WO | WO-2004/069293 | 8/2004 |
| WO | WO-2004/069404 | 8/2004 |
| WO | WO-2004/069915 | 8/2004 |
| WO | WO-2005/080479 | 9/2005 |
| WO | WO-2005/097881 | 10/2005 |
| WO | WO-2006/015729 | 2/2006 |

OTHER PUBLICATIONS

International Search Report in PCT/EP2005/011073 dated Oct. 14, 2005.

*Primary Examiner*—Edward J Cain
(74) *Attorney, Agent, or Firm*—Marshall, Gerstein & Borun LLP

(57) ABSTRACT

The invention relates to finely divided water-absorbing polymeric particles having high fluid transportation and absorption performance, the Centrifuge Retention Capacity (CRC) being not less than 26 g/g, the absorbency under a load of 4.83 kPa (AUL0.7 psi) not less than 23 g/g and the Transportation Value (TV) not less than 15,000 cm$^3$s, the Transportation Value (TV) being the product of Saline Flow Conductivity (SFC) and wicking absorption after 60 minutes (DA$_{60}$) multiplied by 10$^7$, and wherein the wicking absorption after 60 minutes (DA$_{60}$) is the weight of 0.9% by weight sodium chloride solution absorbed by 70 g of the water-absorbing polymeric particles in 60 minutes, wherein the water-absorbing polymeric particles are situated, during measurement, in a circularly round vessel which has an internal diameter of 6 cm and is sealed at its lower end by a sieve base of 36 μm mesh size, and the sieve base is in atmospheric contact with 0.9% by weight sodium chloride solution, processes for their preparation and also their use in hygiene articles and packaging materials.

26 Claims, 2 Drawing Sheets

Fig. 1a - Wicking absorption (side view)
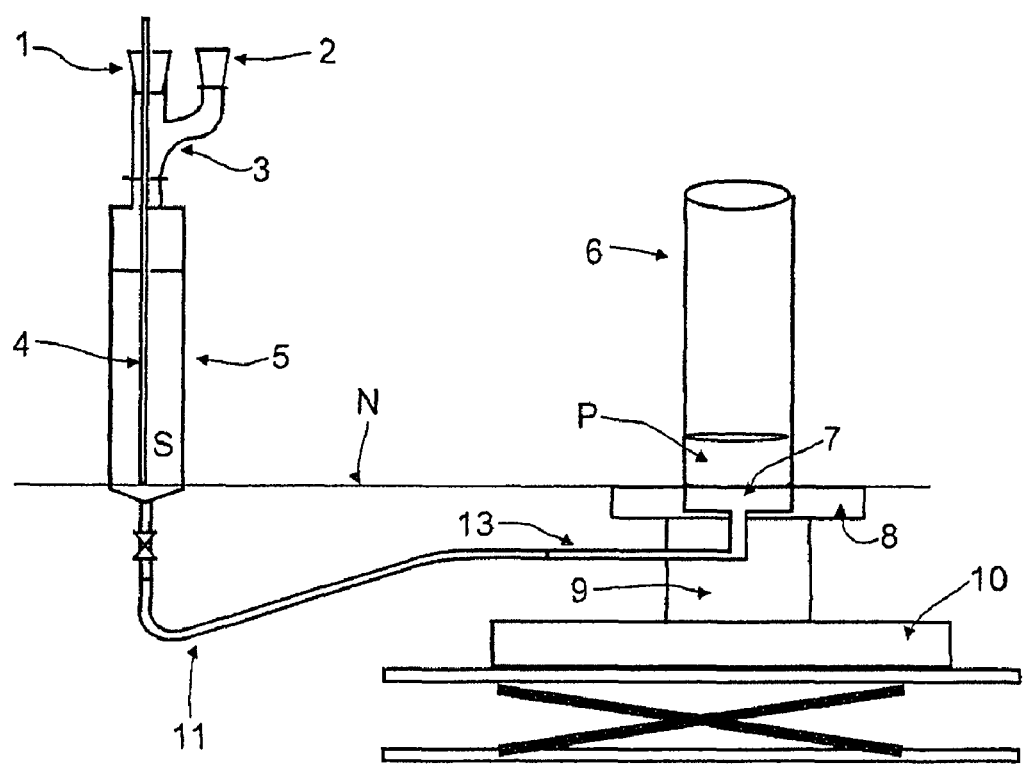

Fig. 1b - Wicking absorption (plan view of balance)
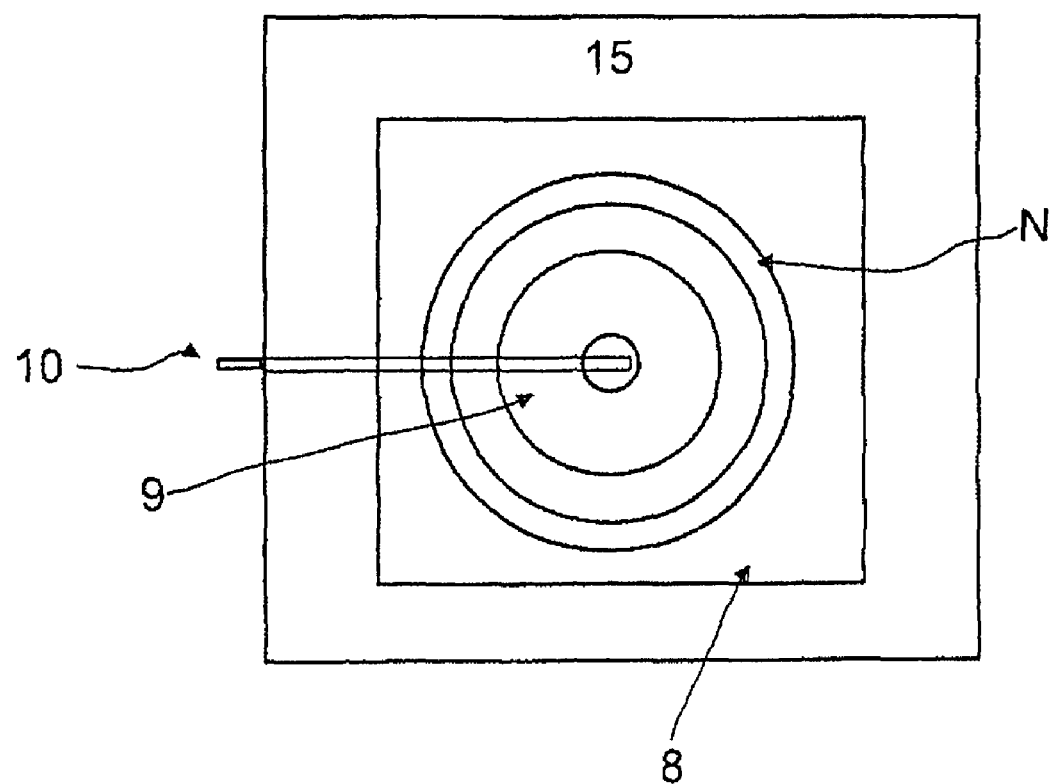

FINE-GRAINED WATER-ABSORBENT PARTICLES WITH A HIGH FLUID TRANSPORT AND ABSORPTION CAPACITY

CROSS-REFERENCE TO RELATED APPLICATIONS

This is the U.S. national phase application of International Application No. PCT/EP2005/011073, filed Oct. 14, 2005, which claims the benefit of German patent application No. 102004051242.6, filed Oct. 20, 2004.

Description

The present invention concerns finely divided water-absorbing polymeric particles with high fluid transportation and absorption performance, processes for their production and also the use in hygiene articles and packaging materials.

Further embodiments of the present invention are discernible from the claims, the description and the examples. It will be appreciated that the hereinbefore identified and the hereinafter still to be more particularly described features of the subject matter of the present invention are utilizable not only in the particular combination indicated but also in other combinations without leaving the realm of the present invention.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, such as guar derivatives for example. Such polymers are used as products capable of absorbing aqueous solutions to manufacture diapers, tampons, sanitary napkins and other hygiene articles, but also as water retaining agents in market gardening.

To improve their performance characteristics, such as for example Saline Flow Conductivity (SFC) in the diaper and Absorbency under Load (AUL), water-absorbing polymeric particles are generally postcrosslinked. This postcrosslinking can be carried out in the aqueous gel phase. But preferably ground and classified (base) polymeric particles are surface coated with a postcrosslinker, dried and thermally postcrosslinked. Useful crosslinkers for this purpose are compounds which comprise two or more groups capable of forming covalent bonds with the carboxylate groups of the hydrophilic polymer.

U.S. Pat. No. 5,599,335 discloses that coarser particles achieve a higher Saline Flow Conductivity (SFC) here for the swollen layer of gel. It is further taught that Saline Flow Conductivity (SFC) can be increased by postcrosslinking, but only always at the expense of the Centrifuge Retention Capacity (CRC) and hence the absorptive capacity of the water-absorbing polymeric particles.

It is common knowledge among those skilled in the art that Saline Flow Conductivity (SFC) can be increased at the expense of Centrifuge Retention Capacity (CRC) by increasing the degree of internal crosslinking (more crosslinker in base polymer) as well as by stronger postcrosslinking (more postcrosslinker).

WO 04/069293 discloses water-absorbing polymeric particles coated with water-soluble salts of polyvalent cations. The polymeric particles possess improved Saline Flow Conductivity (SFC) and improved absorption properties.

WO 04/069404 discloses salt resistant water-absorbing polymeric particles having similar values of Absorbency under Load (AUL) and Centrifuge Retention Capacity (CRC).

WO 04/069915 describes a process for producing water-absorbing polymeric particles which combine high Saline Flow Conductivity (SFC) with strong capillary forces, i.e., the ability to suck up aqueous fluids against the force of gravity. The capillary action of the polymeric particles is achieved through a specific surface finish. To this end, particles less than 180 μm in size are sieved out of the base polymer, agglomerated and combined with the previously removed particles greater than 180 μm.

Ultrathin articles of hygiene require finely divided water-absorbing polymeric particles without coarse particles, since coarse particles would be perceptible and are rejected by the consumer.

But the smaller the particles, the smaller the Saline Flow Conductivity (SFC). On the other hand, small polymeric particles also have smaller pores which improve fluid transportation by wicking absorption within the gel layer.

This is an important factor in ultrathin hygiene articles, since these may comprise construction elements which consist of water-absorbing polymeric particles to an extent which is in the range from 50% to 100% by weight, so that the polymeric particles in use not only perform the storage function for the fluid but also ensure active fluid transportation (wicking absorption) and passive fluid transportation (Saline Flow Conductivity). The greater the proportion of cellulose pulp which is replaced by water-absorbing polymeric particles or synthetic fibers, the greater the number of transportation functions which the water-absorbing polymeric particles have to perform in addition to their storage function.

The present invention therefore has for its object to provide water-absorbing polymeric particles having high Centrifuge Retention Capacity (CRC), high Absorbency under Load (AUL), high active fluid transportation (wicking absorption) and passive fluid transportation (Saline Flow Conductivity), especially a high Saline Flow Conductivity (SFC).

The present invention further has for its object to provide optimized water-absorbing polymeric particles having a low average particle diameter.

The present invention further has for its object to provide a process for producing water-absorbing polymeric particles having high Centrifuge Retention Capacity (CRC), high Absorbency under Load (AUL), high active fluid transportation (wicking absorption) and passive fluid transportation (Saline Flow Conductivity), especially a high Saline Flow Conductivity (SFC).

The present invention further has for its object to provide a process for producing water-absorbing polymeric particles which produces white polymeric particles which are free of noticeable odors, especially when loaded with fluid.

BRIEF DESCRIPTION OF THE DRAWINGS

FIG. 1A is a side view illustrating the apparatus used for testing the wicking absorption of polymeric particles; and FIG. 1B is a plan view illustrating the apparatus used for testing the wicking absorption of polymeric particles.

We have found that this object is achieved by providing water-absorbing polymeric particles comprising
  a) at least one interpolymerized ethylenically unsaturated acid functional monomer,
  b) at least one interpolymerized crosslinker, c) if appropriate one or more interpolymerized ethylenically and/or allylically unsaturated monomers copolymerizable with a),
d) if appropriate one or more water-soluble polymers grafted wholly or partly with the monomers a), b) and if appropriate c), and
e) at least one converted postcrosslinker, wherein the Centrifuge Retention Capacity (CRC) is not less than 26 g/g, the absorbency under a load of 4.83 kPa (AUL 0.7 psi) is not less than 23 g/g and the Transportation Value (TV) is not less than 15,000 cm³s, wherein the Transportation Value (TV) is the product of Saline Flow Conductivity (SFC) and wicking absorption after 60 minutes ($DA_{60}$) multiplied by $10^7$, and wherein the wicking absorption after 60 minutes ($DA_{60}$) is the weight of 0.9% by weight sodium chloride solution absorbed by 70 g of the water-absorbing polymeric particles in 60 minutes, wherein the water-absorbing polymeric particles are situated, during measurement, in a circularly round vessel which has an internal diameter of 6 cm and is sealed at its lower end by a sieve base of 36 μm mesh size, and the sieve base is in atmospheric contact with 0.9% by weight sodium chloride solution.

Centrifuge Retention Capacity is determined by EDANA (European Disposables and Nonwovens Association) recommended test method No. 441.2-02 "Centrifuge retention capacity".

Absorbency under Load is determined by EDANA (European Disposables and Nonwovens Association) recommended test method No. 442.2-02 "Absorption under pressure".

The Transportation Value (TV) is preferably not less than 17,500 cm³s, more preferably not less than 20,000 cm³s, even more preferably not less than 22,500 cm³s, and most preferably not less than 25,000 cm³s, and usually not above 100,000 cm³s.

Preferably less than 2% by weight, more preferably less than 1.5% by weight and most preferably less than 1% by weight of the polymeric particles have a particle size of less than 150 μm. The particle size is determined by EDANA (European Disposables and Nonwovens Association) recommended test method No. 420.2-02 "Particle size distribution".

The acid groups of the interpolymerized monomer a) are preferably more than 60 mol %, more preferably more than 61 mol %, even more preferably more than 62 mol % and most preferably more than 63 mol % and preferably not more than 70 mol %, more preferably not more than 69 mol %, even more preferably not more than 68 mol % and most preferably not more than 67 mol % neutralized.

Suitable monomers for the interpolymerized monomers a), b) and c) are the hereinbelow described monomers i), ii) and iii).

Suitable water-soluble polymers for the at least partly grafted water-soluble polymers d) are the hereinbelow described water-soluble polymers iv).

Suitable postcrosslinkers for the converted postcrosslinkers e) are the hereinbelow described postcrosslinkers v).

The water content of the water-absorbing polymeric particles according to the present invention is preferably less than 6% by weight, more preferably less than 4% by weight and most preferably less than 3% by weight.

Preferred water-absorbing polymeric particles according to the present invention are polymeric particles A, B and C having the abovementioned properties.

Polymeric Particles A:

Preferably less than 2% by weight, more preferably less than 1.5% by weight and most preferably less than 1% by weight of the polymeric particles A have a particle size of above 600 μm.

Preferably not less than 90% by weight, more preferably not less than 95% by weight, even more preferably not less than 98% by weight and most preferably not less than 99% by weight of the polymeric particles A have a particle size in the range from 150 to 600 μm.

Preferably not less than 70% by weight, more preferably not less than 80% by weight, even more preferably not less than 85% by weight and most preferably not less than 90% by weight of the polymeric particles A have a particle size in the range from 300 to 600 μm.

The Centrifuge Retention Capacity (CRC) of the polymeric particles A is usually not less than 26 g/g, preferably not less than 27 g/g, more preferably not less than 28 g/g, even more preferably not less than 29 g/g and most preferably not less than 30 g/g and usually not above 50 g/g.

The absorbency under a load of 4.83 kPa (AUL 0.7 psi) of the polymeric particles A is usually not less than 23 g/g, preferably not less than 24 g/g, more preferably not less than 25 g/g, even more preferably not less than 26 g/g and most preferably not less than 27 g/g and usually not above 45 g/g.

The Saline Flow Conductivity (SFC) of the polymeric particles A is usually not less than $80 \times 10^{-7}$ cm³s/g, preferably not less than $90 \times 10^{-7}$ cm³s/g, more preferably not less than $100 \times 10^{-7}$ cm³s/g, even more preferably not less than $120 \times 10^{-7}$ cm³s/g and most preferably not less than $150 \times 10^{-7}$ cm³s/g and usually not above $500 \times 10^{-7}$ cm³s/g.

Polymeric Particles B:

Preferably less than 2% by weight, more preferably less than 1.5% by weight and most preferably less than 1% by weight of the polymeric particles B have a particle size of above 850 μm.

Preferably not less than 90% by weight, more preferably not less than 95% by weight, even more preferably not less than 98% by weight and most preferably not less than 99% by weight of the polymeric particles B have a particle size in the range from 150 to 850 μm.

Usually not less than 16% by weight, preferably not less than 17% by weight, more preferably not less than 18% by weight, even more preferably not less than 19% by weight and most preferably not less than 20% by weight of the polymeric particles B have a particle size of less than 300 μm.

The Centrifuge Retention Capacity (CRC) of the polymeric particles B is usually more than 28 g/g, not less than 29 g/g, preferably not less than 30 g/g, more preferably not less than 31 g/g, even more preferably not less than 32 g/g and most preferably not less than 33 g/g and usually not above 50 g/g.

The absorbency under a load of 4.83 kPa (AUL 0.7 psi) of the polymeric particles B is usually not less than 23 g/g, preferably not less than 24 g/g, more preferably not less than 25 g/g, even more preferably not less than 26 g/g and most preferably not less than 27 g/g and usually not above 45 g/g.

The Saline Flow Conductivity (SFC) of the polymeric particles B is usually not less than $45 \times 10^{-7}$ cm³s/g, preferably not less than $50 \times 10^{-7}$ cm³s/g, more preferably not less than $60 \times 10^{-7}$ cm³s/g, even more preferably not less than $70 \times 10^{7}$ cm³s/g and most preferably not less than $80 \times 10^{-7}$ cm³s/g and usually not above $500 \times 10^{-7}$ cm³s/g.

The polymeric particles B are preferably coated with a water-insoluble metal phosphate.

As used herein, the term "water-insoluble" denotes a solubility of less than 1 g, preferably of less than 0.1 g and more preferably less than 0.01 g in 100 ml of water at 25° C.

Suitable water-insoluble metal phosphates are for example phosphates which can be deemed to be "phosphates" in the technical sense, such as phosphate oxides, phosphate hydroxides, phosphate silicates, phosphate fluorides or the like.

Preferred water-insoluble metal phosphates are pyrophosphates, hydrogenphosphates and phosphates of calcium, of magnesium, of strontium, of barium, of zinc, of iron, of aluminum, of titanium, of zirconium, of hafnium, of tin, of cerium, of scandium, of yttrium or of lanthanum, and also mixtures thereof.

Preferred phosphates are calcium hydrogenphosphate, calcium phosphate, apatite, Thomas meal, berlinite and Rhenania phosphate. Particular preference is given to calcium hydrogenphosphate, calcium phosphate and apatite, the term "apatite" denoting fluoroapatite, hydroxyl apatite, chloroapatite, carbonate apatite and carbonate fluoroapatite. It will be appreciated that mixtures of various water-insoluble metal phosphates can be used.

The fraction of water-insoluble metal phosphate is usually in the range from 0.001% to 10% by weight, preferably in the range from 0.01% to 5% by weight and more preferably in the range from 0.05% to 2.5% by weight, based on the water-absorbing polymeric particles B.

The Centrifuge Retention Capacity (CRC) of polymeric particles B coated with water-insoluble metal phosphates is usually more than 29 g/g, not less than 30 g/g, preferably not less than 31 g/g, more preferably not less than 32 g/g, even more preferably not less than 33 g/g and most preferably not less than 34 g/g and usually not above 50 g/g.

The absorbency under a load of 4.83 kPa (AUL 0.7 psi) of polymeric particles B coated with water-insoluble metal phosphates is usually not less than 23 g/g, preferably not less than 24 g/g, more preferably not less than 25 g/g, even more preferably not less than 26 g/g and most preferably not less than 27 g/g and usually not above 45 g/g.

The Saline Flow Conductivity (SFC) of polymeric particles B coated with water-insoluble metal phosphates is usually not less than $45 \times 10^{-7}$ cm$^3$s/g, preferably not less than $50 \times 10^{-7}$ cm$^3$s/g, more preferably not less than $60 \times 10^{-7}$ cm$^3$s/g, even more preferably not less than $70 \times 10^{-7}$ cm$^3$s/g and most preferably not less than $80 \times 10^{-7}$ cm$^3$s/g and usually not above $500 \times 10^{-7}$ cm$^3$s/g.

Polymeric Particles C:

Preferably less than 2% by weight, more preferably less than 1.5% by weight and most preferably less than 1% by weight of the polymeric particles C have a particle size of above 850 μm.

Preferably not less than 90% by weight, more preferably not less than 95% by weight, even more preferably not less than 98% by weight and most preferably not less than 99% by weight of the polymeric particles C have a particle size in the range from 150 to 850 μm.

Usually less than 15% by weight, preferably less than 14% by weight, more preferably less than 13% by weight, even more preferably less than 12% by weight and most preferably less than 11% by weight of the polymeric particles C have a particle size of less than 300 μm.

The Centrifuge Retention Capacity (CRC) of the polymeric particles C is usually not less than 30 g/g, preferably not less than 31 g/g, more preferably not less than 32 g/g, even more preferably not less than 33 g/g and most preferably not less than 34 g/g and usually not above 50 g/g.

The absorbency under a load of 4.83 kPa (AUL 0.7 psi) of the polymeric particles C is usually not less than 23 g/g, preferably not less than 24 g/g, more preferably not less than 25 g/g, even more preferably not less than 26 g/g and most preferably not less than 27 g/g and usually not above 45 g/g.

The Saline Flow Conductivity (SFC) of the polymeric particles C is usually not less than $45 \times 10^{-7}$ cm$^3$s/g, preferably not less than $50 \times 10^{-7}$ cm$^3$s/g, more preferably not less than $60 \times 10^{-7}$ cm$^3$s/g, even more preferably not less than $70 \times 10^{-7}$ cm$^3$s/g and most preferably not less than $80 \times 10^{-7}$ cm$^3$s/g and usually not above $500 \times 10^{-7}$ cm$^3$s/g.

The present invention further provides a process for producing water-absorbing polymers by polymerization of a monomer solution comprising i) at least one ethylenically unsaturated acid functional monomer, ii) at least one crosslinker, iii) if appropriate one or more ethylenically and/or allylically unsaturated monomers copolymerizable with i), iv) if appropriate one or more water-soluble polymers grafted wholly or partly with the monomers i), ii) and if appropriate iii), the base polymer obtained being dried, classified, aftertreated with v) at least one postcrosslinker, before being dried and thermally postcrosslinked, which comprises the thermal postcrosslinking being discontinued when the water-absorbing polymeric particles have a Centrifuge Retention Capacity (CRC) of not less than 26 g/g and a Transportation Value (TV) of not less than 15,000 cm$^3$s, wherein the Transportation Value (TV) is the product of Saline Flow Conductivity (SFC) and wicking absorption after 60 minutes (DA$_{60}$) multiplied by $10^7$, and wherein the wicking absorption after 60 minutes (DA$_{60}$) is the weight of 0.9% by weight sodium chloride solution absorbed by 70 g of the water-absorbing polymeric particles in 60 minutes, wherein the water-absorbing polymeric particles are situated, during measurement, in a circularly round vessel which has an internal diameter of 6 cm and is sealed at its lower end by a sieve base of 36 μm mesh size, and the sieve base is in atmospheric contact with 0.9% by weight sodium chloride solution.

Useful monomers i) include for example ethylenically unsaturated carboxylic acids, such as acrylic acid, methacrylic acid, maleic acid, fumaric acid, and itaconic acid, or derivatives thereof, such as acrylamide, methacrylamide, acrylic esters and methacrylic esters. Acrylic acid and methacrylic acid are particularly preferred monomers. Acrylic acid is most preferable.

The water-absorbing polymers are crosslinked, i.e., the addition polymerization is carried out in the presence of compounds having two or more polymerizable groups which can be free-radically interpolymerized into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in German patent application 103 31 450.4, mixed acrylates which, as well as acrylate groups, comprise further ethylenically unsaturated groups, as described in German patent applications 103 31 456.3 and 103 55 401.7, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth) acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention utilizes di(meth)acrylates of polyethylene glycols, the polyethylene glycol used having a molecular weight between 300 and 1000.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether 40-tuply ethoxylated glycerol and also of altogether 40-tuply ethoxylated trimethylolpropane.

Very particularly preferred for use as crosslinkers ii) are diacrylated, dimethacrylated, triacrylated or trimethacrylated multiply ethoxylated and/or propoxylated glycerols as described for example in prior German patent application DE 103 19 462.2. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 ppm) in the water-absorbing polymer and the aqueous extracts of water-absorbing polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols or polyacrylic acids, preferably polyvinyl alcohol and starch.

The preparation of a suitable base polymer and also further useful hydrophilic ethylenically unsaturated monomers i) are described in DE-A 199 41 423, EP-A 686 650, WO 01/45758 and WO 03/104300.

The reaction is preferably carried out in a kneader as described for example in WO 01/38402, or on a belt reactor as described for example in EP-A 955 086.

The acid groups of the hydrogels obtained are preferably more than 60 mol %, more preferably more than 61 mol %, even more preferably more than 62 mol % and most preferably more than 63 mol % and preferably not more than 70 mol %, more preferably not more than 69 mol %, even more preferably not more than 68 mol % and most preferably not more than 67 mol % neutralized, for which the customary neutralizing agents can be used, for example ammonia, amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metals, but most preference is given to sodium hydroxide, sodium carbonate or sodium bicarbonate and also mixtures thereof. Typically, neutralization is achieved by admixing the neutralizing agent as an aqueous solution or else preferably as a solid material.

Neutralization can be carried out after polymerization, at the hydrogel stage. But it is also possible to neutralize up to 40 mol %, preferably from 10 to 30 mol % and more preferably from 15 to 25 mol % of the acid groups before polymerization by adding a portion of the neutralizing agent to the monomer solution and to set the desired final degree of neutralization only after polymerization, at the hydrogel stage. The monomer solution may be neutralized by admixing the neutralizing agent, either to a predetermined degree of preneutralization with subsequent postneutralization to the final value after or during the polymerization reaction, or the monomer solution is directly adjusted to the final value by admixing the neutralizing agent before polymerization. The hydrogel can be mechanically comminuted, for example by means of a meat grinder, in which case the neutralizing agent can be sprayed, sprinkled or poured on and then carefully mixed in. To this end, the gel mass obtained can be repeatedly minced for homogenization.

A degree of neutralization which is too low gives rise to unwanted thermal crosslinking effects in the course of the subsequent drying and also during the subsequent postcrosslinking of the base polymer which are able to reduce the Centrifuge Retention Capacity (CRC) of the water-absorbing polymer substantially, to the point of inutility.

When the degree of neutralization is too high, however, postcrosslinking will be less efficient, which leads to a reduced Saline Flow Conductivity (SFC) on the part of the swollen hydrogel.

An optimum result is obtained when the degree of neutralization of the base polymer is adjusted such as to achieve efficient postcrosslinking and thus a high Saline Flow Conductivity (SFC) while at the same time neutralization is carried on sufficiently for the hydrogel being produced to be dryable in a customary belt dryer, or other drying apparatuses customary on an industrial scale, without loss of Centrifuge Retention Capacity (CRC).

The neutralized hydrogel is then dried with a belt, fluidized bed, shaft or drum dryer until the residual moisture content is preferably below 10% by weight and especially below 5% by weight, the water content being determined by EDANA (European Disposables and Nonwovens Association) recommended test method No. 430.2-02 "Moisture content". The dried hydrogel is subsequently ground and sieved, useful grinding apparatus typically including roll mills, pin mills or swing mills, the sieves employed having mesh sizes necessary to produce the water-absorbing polymeric particles A, B and C.

The base polymers are subsequently postcrosslinked. Useful postcrosslinkers v) are compounds comprising two or more groups capable of forming covalent bonds with the carboxylate groups of the polymers. Useful compounds are for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, DE-C 35 23 617 and EP-A 450 922, or β-hydroxyalkylamides as described in DE-A 102 04 938 and U.S. Pat. No. 6,239,230. It is also possible to use compounds of mixed functionality, such as glycidol, 3-ethyl-3-oxetanemethanol (trimethylolpropaneoxetane), as described in EP-A 1 199 327, aminoethanol, diethanolamine, triethanolamine or compounds which develop a further functionality after the first reaction, such as ethylene oxide, propylene oxide, isobutylene oxide, aziridine, azetidine or oxetane.

Useful postcrosslinkers v) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by German patent application 103 34 584.1 bicyclic amide acetals, by EP-A 1 199 327 oxetanes and cyclic ureas and by WO 03/031482 morpholine-2,3-dione and its derivatives.

Postcrosslinking is typically carried out by spraying a solution of the postcrosslinker onto the hydrogel or the dry base-polymeric particles. Spraying is followed by thermal drying, and the postcrosslinking reaction can take place not only before but also during drying.

Preferred postcrosslinkers v) are amide acetals or carbamic esters of the general formula I $$R^1\text{—O—}\underset{R^3}{\underset{|}{\overset{R^2}{\overset{|}{C}}}}\text{—}\underset{R^5}{\underset{|}{N}}\text{—}R^4 \quad (I)$$

where
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl
$R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen common to $R^2$ and $R^3$, wherein $R^1$ and $R^4$ and/or $R^5$ and $R^6$ can be a bridged $C_2$-$C_6$-alkanediyl and wherein the abovementioned radicals $R^1$ to $R^6$ can still have in total one to two free valences and can be attached through these free valences to at least one suitable basic structure, or polyhydric alcohols, in which case the molecular weight of the polyhydric alcohol is preferably less than 100 g/mol, preferably less than 90 g/mol, more preferably less than 80 g/mol and most preferably less than 70 g/mol per hydroxyl group and the polyhydric alcohol has no vicinal, geminal, secondary or tertiary hydroxyl groups, and polyhydric alcohols are either diols of the general formula IIa $$HO\text{—}R^6\text{—}OH \quad (IIa)$$

where $R^6$ is either an unbranched dialkyl radical of the formula $-(CH_2)_n-$, where n is an integer from 3 to 20 and preferably from 3 to 12, although 4 is less preferable, and both the hydroxyl groups are terminal, or an unbranched, branched or cyclic dialkyl radical or polyols of the general formula IIb $$R^7\text{—}\underset{R^{10}}{\underset{|}{\overset{R^8}{\overset{|}{C}}}}\text{—}R^9 \quad (IIb)$$

where $R^7$, $R^8$, $R^9$ and $R^{10}$ are independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and in total 2, 3 or 4 and preferably 2 or 3 hydroxyl groups are present, and not more than one of $R^7$, $R^8$, $R^9$ and $R^{10}$ is hydroxyl, or cyclic carbonates of the general formula III $$\text{(III)}$$

where $R^{11}$, $R^{12}$, $R^{13}$, $R^{14}$, $R^{15}$ and $R^{16}$ are independently hydrogen, methyl, ethyl, n-propyl, isopropyl, n-butyl, sec-butyl or isobutyl, and n is either 0 or 1, or bisoxazolines of the general formula IV $$\text{(IV)}$$

where $R^{17}$, $R^{18}$, $R^{19}$, $R^{20}$, $R^{21}$, $R^{22}$, $R^{23}$ and $R^{24}$ are independently hydrogen, methyl, ethyl, n-propyl, isopropyl, n-butyl, sec-butyl or isobutyl and $R^{25}$ is a single bond, a linear, branched or cyclic $C_1$-$C_{12}$-dialkyl radical or polyalkoxydiyl radical which is constructed of one to ten ethylene oxide and/or propylene oxide units, and is possessed by polyglycoldicarboxylic acids for example.

Preferred postcrosslinkers v) are extremely selective. Byproducing and secondary reactions which lead to volatile and hence malodorous compounds are minimized. The water-absorbing polymers produced with preferred postcrosslinkers v) are therefore odor neutral even in the moistened state.

Epoxy compounds, by contrast, may at high temperatures in the presence of suitable catalysts undergo various rearrangement reactions which lead to aldehydes or ketones for example. These can then undergo further secondary reactions which eventually lead to the formation of malodorous impurities which are undesirable in hygiene articles on account of their odor. Therefore, epoxy compounds are less suitable for postcrosslinking above a temperature of about 140 to 150° C. Amino- or imino-comprising postcrosslinkers v) will at similar temperatures undergo even more involved rearrangement reactions which tend to give rise to malodorous trace impurities and brownish product discolorations.

Polyhydric alcohols employed as postcrosslinkers v) require high postcrosslinking temperatures on account of their low reactivity. Alcohols comprising vincinal, geminal, secondary and tertiary hydroxyl groups, when employed as postcrosslinkers, give rise to byproducts which are undesirable in the hygiene sector because they lead to unpleasant odors and/or discolorations of the corresponding hygiene article during manufacture or use.

Preferred postcrosslinkers v) of the general formula I are 2-oxazolidones, such as 2-oxazolidone and N-hydroxyethyl-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxa-bicyclo[3.3.0]octane and 5-isopropyl-1-aza-4,6-dioxabicyclo[3.3.0]octane, bis-2-oxazolidones and poly-2-oxazolidones.

Particularly preferred postcrosslinkers v) of the general formula I are 2-oxazolidone, N-methyl-2-oxazolidone, N-hydroxyethyl-2-oxazolidone and N-hydroxypropyl-2-oxazolidone.

Preferred postcrosslinkers v) of the general formula IIa are 1,3-propanediol, 1,5-pentanediol, 1,6-hexanediol and 1,7-heptanediol. Further examples of postcrosslinkers of the formula IIa are 1,3-butanediol, 1,8-octanediol, 1,9-nonanediol and 1,10-decanediol.

The diols IIa are preferably soluble in water in that the diols of the general formula IIa dissolve in water at 23° C. to an extent of not less than 30% by weight, preferably not less than 40% by weight, more preferably not less than 50% by weight and most preferably not less than 60% by weight, examples being 1,3-propanediol and 1,7-heptanediol. Even more preference is given to such postcrosslinkers as are liquid at 25° C.

Preferred postcrosslinkers v) of the general formula IIb are 1,2,3-butanetriol, 1,2,4-butanetriol, glycerol, trimethylolpropane, trimethylolethane, pentaerythritol, ethoxylated glycerol, trimethylolethane or trimethylolpropane each having 1 to 3 ethylene oxide units per molecule, propoxylated glycerol, trimethylolethane or trimethylolpropane each having 1 to 3 propylene oxide units per molecule. Preference is further given to 2-tuply ethoxylated or propoxylated neopentylglycol. Particular preference is given to 2-tuply and 3-tuply ethoxylated glycerol and trimethylolpropane.

Preferred polyhydric alcohols IIa and IIb have a 23° C. viscosity of less than 3000 mPas, preferably less than 1500 mPas, more preferably less than 1000 mPas, even more preferably less than 500 mPas and most preferably less than 300 mPas.

Particularly preferred postcrosslinkers v) of the general formula III are ethylene carbonate and propylene carbonate.

A particularly preferred postcrosslinker v) of the general formula IV is 2,2'-bis(2-oxazoline).

The at least one postcrosslinker v) is typically used in an amount of not more than 0.30% by weight, preferably not more than 0.15% by weight and more preferably in the range from 0.001% to 0.095% by weight, all percentages being based on the base polymer, as an aqueous solution.

It is possible to use a single postcrosslinker v) from the above selection or any desired mixtures of various postcrosslinkers.

The aqueous postcrosslinking solution, as well as the at least one postcrosslinker v), can typically further comprise a cosolvent.

Cosolvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol or 1,4-butanediol, ketones, such as acetone, or carboxylic esters, such as ethyl acetate. The disadvantage with many of these cosolvents is that they have characteristic intrinsic odors.

The cosolvent itself is ideally not a postcrosslinker under the reaction conditions. However, in a borderline case and depending on the residence time and the temperature, the cosolvent may to some extent contribute to crosslinking. This will be the case in particular when the postcrosslinker v) is relatively inert and therefore is itself able to form its cosolvent, as with the use for example of cyclic carbonates of the general formula II, diols of the general formula IIa or polyols of the general formula IIb. Such postcrosslinkers v) can also be used as cosolvent when admixed with more reactive postcrosslinkers v), since the actual postcrosslinking reaction can then be carried out at lower temperatures and/or shorter residence times than in the absence of the more reactive crosslinker v). Since the cosolvent is used in relatively large amounts and will also remain to some extent in the product, it must not be toxic.

The diols of the general formula IIa, the polyols of the general formula IIb and also the cyclic carbonates of the general formula III are also useful as cosolvents in the process of the present invention. They perform this function in the presence of a reactive postcrosslinker v) of the general formula I and/or IV and/or of a di- or triglycidyl crosslinker. However, preferred cosolvents in the process of the present invention are in particular the diols of the general formula IIa, especially when the hydroxyl groups are sterically hindered by neighboring groups from participating in a reaction. Such diols are in principle also useful as postcrosslinkers v), but for this require distinctly higher reaction temperatures or if appropriate higher use levels than sterically unhindered diols. Useful sterically hindered and hence reaction inert diols also include diols having tertiary hydroxyl groups.

Examples of such sterically hindered diols of the general formula IIa which are therefore particularly preferred for use as a cosolvent are 2,2-dimethyl-1,3-propanediol (neopentylglycol), 2-ethyl-1,3-hexanediol, 2-methyl-1,3-propanediol and 2,4-dimethylpentane-2,4-diol.

Particularly preferred cosolvents in the process of the present invention further include the polyols of the general formula IIb. Among these, the 2- to 3-tuply alkoxylated polyols are preferred in particular. But particularly useful cosolvents further include 3- to 15-tuply and most particularly 5- to 10-tuply ethoxylated polyols based on glycerol, trimethylolpropane, trimethylolethane or pentaerythritol. Seven-tuply ethoxylated trimethylolpropane is particularly useful.

Useful cosolvents further include di(trimethylolpropane) and also 5-ethyl-1,3-dioxane-5-methanol.

Particularly preferred combinations of less reactive postcrosslinker v) as cosolvent and reactive postcrosslinker v) are combinations of preferred polyhydric alcohols, diols of the general formula IIa and polyols of the general formula IIb, with amide acetals or carbamic esters of the general formula I.

Very particularly preferred combinations are 2-oxazolidone/1,3-propanediol and N-(2-hydroxyethyl)-2-oxazolidone/1,3-propanediol.

Very particularly preferred combinations further include 2-oxazolidone or N-(2-hydroxyethyl)-2-oxazolidone as a reactive crosslinker combined with 1,5-pentanediol or 1,6-hexanediol or 2-methyl-1,3-propanediol or 2,2-dimethyl-1,3-propanediol, dissolved in water and/or isopropanol as nonreactive solvent.

The boiling point of the at least one postcrosslinker v) is preferably no higher than 160° C., more preferably no higher than 140° C. and most preferably no higher than 120° C. or preferably no lower than 200° C., more preferably no lower than 220° C. and most preferably no lower than 250° C.

The boiling point of cosolvent is preferably no higher than 160° C., more preferably no higher than 140° C. and most preferably no higher than 120° C. or preferably no lower than 200° C., more preferably no lower than 220° C. and most preferably no lower than 250° C.

Particularly useful cosolvents in the process of the present invention therefore also include those which form a low boiling azeotrope with water or with a second cosolvent. The boiling point of this azeotrope is preferably no higher than 160° C., more preferably no higher than 140° C. and most preferably no higher than 120° C. Water vapor volatile cosolvents are likewise very useful, since they can be wholly or partly removed with the water evaporating in the course of drying.

Postcrosslinkers v) and cosolvents having a mid range boiling point surprisingly lead to water-absorbing polymeric particles having an undesirable chemical odor.

The concentration of cosolvent in the aqueous postcrosslinker solution is frequently in the range from 15% to 50% by weight, preferably in the range from 15% to 40% by weight and more preferably in the range from 20% to 35% by weight, based on the postcrosslinker solution. In the case of cosolvents having a but limited miscibility with water, it will be advantageous to adjust the aqueous postcrosslinker solution such that there is only one phase, if appropriate by lowering the concentration of cosolvent.

A preferred embodiment does not utilize any cosolvent. The at least one postcrosslinker v) is then only employed as a solution in water, with or without an added deagglomerating assistant.

The concentration of the at least one postcrosslinker v) in the aqueous postcrosslinker solution is for example in the range from 1% to 20% by weight, preferably in the range from 1.5% to 10% by weight and more preferably in the range from 2% to 5% by weight, based on the postcrosslinker solution.

The total amount of postcrosslinker solution based on base polymer is usually in the range from 0.3% to 15% by weight and preferably in the range from 2% to 6% by weight.

In a preferred embodiment, the base polymer is admixed with a surfactant deagglomerating assistant, for example a sorbitan monoester, such as sorbitan mono-cocoate and sorbitan monolaurate, or ethoxylated variants thereof. Very useful deagglomerating assistants further include the ethoxylated and alkoxylated derivatives of 2-propylheptanol, which are marketed by BASF AG of Germany under the brandnames of Lutensol XL® and Lutensol XP®. The deagglomerating assistant can be added separately or to the postcrosslinker solution. Preferably the deagglomerating assistant is added to the postcrosslinker solution.

The useful level of deagglomerating assistant based on base polymer is for example in the range from 0% to 0.01% by weight, preferably in the range from 0% to 0.005% by weight and more preferably in the range from 0% to 0.002% by weight. The deagglomerating assistant is preferably dosed such that the surface tension of an aqueous extract of the swollen base polymer and/or of the swollen postcrosslinked water-absorbing polymer is not less than 0.060 N/m, preferably not less than 0.062 N/m and more preferably not less than 0.065 N/m and advantageously not more than 0.072 N/m, at 23° C.

The dried base polymer used in the process of the present invention typically has a residual moisture content in the range from 0% to 13% by weight and preferably in the range from 2% to 9% by weight after drying and before application of the postcrosslinking solution. Optionally, however, this moisture content can also be raised up to 75% by weight, for example by applying water in an upstream spraying mixer. The moisture content is determined by EDANA (European Disposables and Nonwovens Association) recommended test method No. 430.2-02 "Moisture content". Such an increase in the moisture content leads to a slight preswelling of the base polymer and improves the distribution of the crosslinker on the surface and also the penetration through the particles.

Spray nozzles useful in the process of the present invention are not subject to any restriction. Such nozzles can be pressure fed with the liquid to be spray dispensed. The atomizing of the liquid to be spray dispensed can in this case be effected by decompressing the liquid in the nozzle bore after the liquid has reached a certain minimum velocity. Also useful are one-material nozzles, for example slot nozzles or swirl or whirl chambers (full cone nozzles) (available for example from Düsen-Schlick GmbH, Germany or from Spraying Systems Deutschland GmbH, Germany). Such nozzles are also described in EP-A-0 534 228 and EP-A-1 191 051.

After spraying, the polymeric powder is thermally dried, and the postcrosslinking reaction can take place before, during or after drying.

The spraying with the solution of postcrosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers.

Contact dryers are preferable, shovel dryers more preferable and disk dryers most preferable as apparatus in which thermal drying is carried out. Suitable dryers include for example Bepex® dryers and Nara® dryers. Fluidized bed dryers can be used as well.

Drying can take place in the mixer itself, for example by heating the jacket or introducing a stream of warm air. It is similarly possible to use a downstream dryer, for example a tray dryer, a rotary tube oven or a heatable screw. But it is also possible for example to utilize an azeotropic distillation as a drying process.

It is particularly preferable to apply the solution of postcrosslinker in a high speed mixer, for example of the Schugi-Flexomix® or Turbolizer® type, to the base polymer and the latter can then be thermally postcrosslinked in a reaction dryer, for example of the Nara-Paddle-Dryer® type or a disk dryer. The base polymer used can still have a temperature in the range from 10 to 120° C. from preceding operations, and the postcrosslinking solution can have a temperature in the range from 0 to 150° C. More particularly, the postcrosslinking solution can be heated to lower the viscosity. The preferred postcrosslinking and drying temperature range is from 30 to 220° C., especially from 150 to 210° C. and most preferably from 160 to 190° C. The preferred residence time at this temperature in the reaction mixer or dryer is below 100 minutes, more preferably below 70 minutes and most preferably below 40 minutes.

The postcrosslinking dryer is flushed with air to remove vapors during the drying and postcrosslinking reaction. To augment the drying process, the dryer and the attached assemblies are ideally fully heated.

Cosolvents removed with the vapors may of course be condensed again outside the reaction dryer and if appropriate recycled.

After the reactive drying step has been concluded, the dried water-absorbing polymeric particles are cooled. To this end, the warm and dry polymer is preferably continuously transferred into a downstream cooler. This can be for example a disk cooler, a Nara paddle cooler or a screw cooler. Cooling is via the walls and if appropriate the stirring elements of the cooler, through which a suitable cooling medium such as for example warm or cold water flows. Water or aqueous solutions of additives may preferably be sprayed on in the cooler; this increases the efficiency of cooling (partial evaporation of water) and the residual moisture content in the finished product can be adjusted to a value in the range from 0% to 6% by weight, preferably in the range from 0.01% to 4% by weight and more preferably in the range from 0.1% to 3% by weight. The increased residual moisture content reduces the dust content of the product.

Optionally, however, it is possible to use the cooler for cooling only and to carry out the addition of water and additives in a downstream separate mixer. Cooling stops the reaction by lowering the temperature to below the reaction temperature and the temperature needs altogether only to be lowered to such an extent that the product is easily packable into plastic bags or into silo trucks.

The water-absorbing polymeric particles can be coated with water-insoluble metal phosphates as described in WO 02/060983.

To this end, the water-insoluble metal phosphates can be added as a powder or as a dispersion in a suitable dispersion medium, water being an example.

When the water-insoluble metal phosphates are used and sprayed in the form of dispersions, they are preferably used as aqueous dispersions, and it is preferable to additionally apply a dustproofing agent to fix the additive to the surface of the water-absorbing polymer. The applying of the dustproofing agent and of the dispersion is preferably effected together with the postcrosslinking solution and can if appropriate take place from a conjoint solution or from a plurality of separate solutions via separate nozzle systems at the same time or at different times. Preferred dustproofing agents are dendritic polymers, highly branched polymers, such as polyglycerines, polyethylene glycols, polypropylene glycols, random or block copolymers of ethylene oxide and propylene oxide. Useful dustproofing agents for this purpose further include the polyethoxylates or polypropoxylates of polyhydroxy compounds, as of glycerol, sorbitol, trimethylolpropane, trimethylolethane and pentaerythritol. Examples thereof are n tuply ethoxylated trimethylolpropane or glycerol, n representing an integer between 1 and 100. Further examples are block copolymers, such as altogether n tuply ethoxylated and then m tuply propoxylated trimethylolpropane or glycerol, n representing an integer between 1 and 40 and m representing an integer between 1 and 40. The order of the blocks can also be reversed.

The water-insoluble metal phosphates have an average particle size of usually less than 400 µm, preferably less than 100 µm, more preferably less than 50 µm, even more preferably less than 10 µm and most preferably in the particle size range from 2 to 7 µm.

But it is also possible for the water-insoluble metal phosphates to be formed in situ on the surface of the water-absorbing polymeric particles. To this end, solutions of phosphoric acid or of soluble phosphates and solutions of soluble metal salts are separately sprayed on, the water-insoluble metal phosphate forming and depositing on the particle surface.

Coating with the water-insoluble metal phosphate can be carried out before, during or after the postcrosslinking step.

The water-absorbing polymeric particles B are preferably coated with water-insoluble metal phosphates.

The water-absorbing polymeric particles B have a higher fraction of polymeric particles less than 300 µm in particle size. Saline Flow Conductivity (SFC) decreases with particle size. Saline Flow Conductivity (SFC) can be increased by coating with water-insoluble metal phosphates, with water-insoluble metal phosphates being distinctly superior to other possible inorganic additives. Since Saline Flow Conductivity (SFC) and Centrifuge Retention Capacity (CRC) mutually influence each other, the addition of water-insoluble metal phosphates can also be used alternatively to increase Centrifuge Retention Capacity (CRC) while keeping Saline Flow Conductivity (SFC) the same.

Optionally, however, all known coatings, such as film forming polymers, dendrimers, polycationic polymers (such as polyvinylamine, polyethyleneimine or polyallylamine), water-insoluble polyvalent metal salts, such as calcium sulfate, water-soluble polyvalent metal salts, such as aluminum sulfate, calcium or magnesium salts, or water-soluble zirconium salts, or hydrophilic inorganic particles, such as clay minerals, pyrogenic silica, alumina and magnesia, can be additionally applied. This makes it possible to achieve additional effects, such as a reduced tendency to cake, improved processing properties or a further enhanced Saline Flow Conductivity (SFC). When the additives are used and sprayed in the form of dispersions, they are preferably used as aqueous dispersions, and it is preferable to additionally apply a dust-proofing agent to fix the additive on the surface of the water-absorbing polymer.

The process of the present invention is a simple way to obtain water-absorbing polymeric particles possessing good fluid transportation properties and good absorption performance. It is not necessary for example for the base polymer prior to postcrosslinking to be admixed with agglomerates, such as not less than 10% by weight of agglomerates composed of base polymer particles.

It is similarly unnecessary to make the base polymers by using alkali metal silicates for partial or complete neutralization.

Nor is there any need to aftertreat the base polymer with polyvalent metal ions, such as aluminum ions as aluminum sulfate solution.

The addition of solid powders, especially of water-soluble polyvalent metal salts, examples being aluminum salts, such as aluminum sulfate, potassium alum, aluminum nitrate, aluminum chloride or sodium alum, is unnecessary, especially since the salt particles only act as spacers between the polymeric particles and thus briefly raise flow conductivity before they dissolve. Such spacers have no positive effect on porosity and hence on the wicking absorption of the water-absorbing polymeric particles.

The addition of hydrophilic inorganic particles, examples being clay minerals and pyrogenic silica, alumina and magnesia, likewise only leads to an increased Saline Flow Conductivity (SFC) without improving the wicking absorption.

This is a particular advantage of the process according to the present invention, since there is no need for additional equipment, as for the application of coatings for example.

The polymers of the present invention are notable for a high wicking absorption. Wicking absorption can be determined using the wicking absorption test described hereinbelow. High wicking absorption manifests itself by a high initial absorption and also a high fluid uptake after 60 and 240 minutes. Particularly good superabsorbent polymers are additionally notable for the fact that a further fluid uptake takes place even after more than 150 minutes.

In the atmospheric wicking absorption test, the amount of 0.9% by weight sodium chloride solution taken up by the polymers of the present invention is preferably not less than 250 g and more preferably not less than 300 g within 60 minutes and preferably not less than 300 g and more preferably not less than 350 g within 240 minutes.

When the wicking absorption test is carried out at a pressure of 0.3 psi (2070 Pa), the amount of 0.9% by weight sodium chloride solution taken up by the polymers of the present invention is preferably not less than 100 g and more preferably not less than 150 g within 60 minutes and preferably not less than 115 g and more preferably not less than 125 g within 240 minutes.

When the wicking absorption test is carried out at a pressure of 0.7 psi (4830 Pa), the amount of 0.9% by weight sodium chloride solution taken up by the polymers of the present invention within 60 minutes is preferably not less than 50 g, more preferably not less than 60 g and even more preferably not less than 70 g.

The polymers of the present invention are further notable for the fact that wicking absorption and flow conductivity are both optimized such that the product of these two parameters is optimized for fluid transportation. This product of Saline Flow Conductivity (SFC) and wicking absorption after 60 min ($DA_{60}$) multiplied by $10^7$ is referred to as the Transportation Value (TV) and is calculated according to the formula indicated below.

Centrifuge Retention Capacity (CRC) and Saline Flow Conductivity (SFC) are optimized via the degree of neutralization of the base polymer while Centrifuge Retention Capacity (CRC) and Transportation Value (TV) are optimized via the reaction conditions during postcrosslinking. More particularly, polymeric particles with a low degree of postcrosslinking generally have a high Centrifuge Retention Capacity (CRC) and a low Transportation Value (TV) while highly postcrosslinked polymeric particles generally have a low Centrifuge Retention Capacity (CRC) and a high Transportation Value (TV), the extent of postcrosslinking also being determined via the reaction temperature and the reaction time.

Furthermore, the water-absorbing polymeric particles of the present invention are substantially free of compounds which lead to unpleasant odors especially during use.

The water-absorbing polymeric particles of the present invention are very white, which is necessary especially in ultrathin diapers having a high fraction of water-absorbing polymeric particles. Even minimal color variations are visible through the thin topsheet of an ultrathin diaper which is not accepted by customers.

The present invention further provides hygiene articles comprising water-absorbing polymeric particles according to the present invention, preferably ultrathin diapers comprising an absorbent layer consisting of 50% to 100% by weight, preferably 60% to 100% by weight, more preferably 70% to 100% by weight, even more preferably 80% to 100% by weight and most preferably 90% to 100% by weight of water-absorbing polymeric particles according to the present invention, the closure surrounding the absorbent layer not included of course.

The water-absorbing polymeric particles of the present invention are also very advantageous for producing laminates and composite structures as described for example in US-A 2003/0181115 and US-A 2004/0019342. As well as the hotmelt adhesives described in the two references for producing such novel absorbent structures, and especially the hotmelt adhesive fibers which are described in US-A 2003/0181115 and to which the water-absorbing polymeric particles are bound, the water-absorbing polymeric particles of the present invention are also useful for producing completely analogous structures by utilizing UV crosslinkable hotmelt adhesives which are marketed for example as AC-Resin® (BASF AG, Germany). These UV crosslinkable hotmelt adhesives have the advantage of being processable at as low as 120 to 140° C.; therefore, they have better compatibility with many thermoplastic substrates. It is a further significant advantage that UV crosslinkable hotmelt adhesives are generally recognized as very safe by toxicologists and do not cause any outgassing in hygiene articles. A very significant advantage in connection with the water-absorbing polymeric particles of the present invention is the property of UV crosslinkable hotmelt adhesives not to yellow during processing and crosslinking.

This is advantageous especially when ultrathin or partially transparent hygiene articles are to be produced. The combination of the water-absorbing polymeric particles of the present invention with UV crosslinkable hotmelt adhesives is therefore particularly advantageous. Suitable UV crosslinkable hotmelt adhesives are described for example in EP-A 377 199, EP-A 445 641, U.S. Pat. No. 5,026,806, EP-A 655 465 and EP-A 377 191.

To determine the quality of postcrosslinking, the dried water-absorbing polymeric particles are tested using the test methods described hereinbelow.

Methods:

The measurements should be carried out, unless otherwise stated, at an ambient temperature of 23±2° C. and a relative humidity of 50±10%. The water-absorbing polymeric particles are thoroughly mixed through before measurement.

Centrifuge Retention Capacity (CRC)

Centrifuge Retention Capacity is determined by EDANA (European Disposables and Nonwovens Association) recommended test method No. 441.2-02 "Centrifuge retention capacity", except that for each example the actual sample having the particle size distribution reported in the example is measured.

Absorbency Under Load (AUL)

Absorbency under Load is determined by EDANA (European Disposables and Nonwovens Association) recommended test method No. 442.2-02 "Absorption under pressure", except that for each example the actual sample having the particle size distribution reported in the example is measured.

Saline Flow Conductivity (SFC)

The flow conductivity of a swollen layer of gel under a confining pressure of 0.3 psi (2070 Pa) is determined as described in EP-A 640 330 as the Gel Layer Permeability of a swollen gel layer of water-absorbing polymeric particles, although the apparatus described in the aforementioned patent application at page 19 and FIG. 8 was modified to the effect that the glass frit (40) was no longer used, the piston

(39) is made of the same plastics material as the cylinder (37) and now comprises 21 equally sized holes uniformly distributed over the entire contact surface. The procedure and evaluation of the measurement remains unchanged compared to EP-A 640 330. The flow rate is automatically recorded.

Saline Flow Conductivity (SFC) is calculated as follows:

$$SFC[cm^3 s/g] = (Fg(t=0) \times L0)/(d \times A \times WP),$$

where Fg(t=0) is the flow rate of NaCl solution in g/s obtained from a linear regression analysis of the Fg(t) data of the flow rate determinations by extrapolation to t=0, L0 is the thickness of the gel layer in cm, d is the density of the NaCl solution in $g/cm^3$, A is the area of the gel layer in $cm^2$ and WP is the hydrostatic pressure on the gel layer in $dyn/cm^2$.

16 h Extractables

The level of extractable constituents in the water-absorbing polymeric particles is determined by the EDANA (European Disposables and Nonwovens Association) recommended test method No. 470.2-02 "Determination of extractable polymer content by potentiometric titration".

pH Value

The pH of the water-absorbing polymeric particles is determined by the EDANA (European Disposables and Nonwovens Association) recommended test method No. 400.2-02 "Determination of pH".

Free Swell Rate (FSR)

1.00 g (=W1) of the dry water-absorbing polymeric particles is weighed into a 25 ml glass beaker and is uniformly distributed on the base of the glass beaker. 20 ml of a 0.9% by weight sodium chloride solution are then dispensed into a second glass beaker, the contents of this beaker are rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR[g/gs] = W2/(W1 \times t)$$

When the moisture content of the hydrogel-forming polymer is more than 3% by weight, however, the weight W1 must be corrected for this moisture content.

Surface Tension of Aqueous Extract 0.50 g of the water-absorbing polymeric particles is weighed into a small glass beaker and admixed with 40 ml of 0.9% by weight salt solution. The contents of the beaker are magnetically stirred at 500 rpm for 3 minutes and then allowed to settle for 2 minutes. Finally, the surface tension of the supernatant aqueous phase is measured with a K10-ST digital tensiometer or a comparable apparatus having a platinum plate (from Kruess). The measurement is carried out at a temperature of 23° C.

Moisture Content of Hydrogel

The water content of the water-absorbing polymeric particles is determined by the EDANA (European Disposables and Nonwovens Association) recommended test method No. 430.2-02 "Moisture content".

Wicking Absorption

Experimental Setup:

Setup of apparatus as depicted in FIG. 1a (side view) and FIG. 1b (plan view):

A cylindrical 1,000 ml dropping funnel (German standard specification DIN 12566 graduated, with standard 29/32, female ground joint, tap with hollow glass stopcock and exit tube of Duran glass, scale division: 20 ml, height 39.5 cm, manufacturer: Heico) with two neck adapter of Duran glass, with standard 19/26 and 29/32 ground joints (11 cm high) is filled with 1,000 ml of 0.9% sodium chloride solution. A glass tube (47 cm long, internal diameter: 1.5 mm, external diameter: 4 mm) is then inserted as deeply as possible into the dropping funnel. The glass tube is sealed off against the external atmosphere on one of the openings of the two neck adapter using a bored rubber bung (or a screw seal).

A balance connected to a computer is placed on a lifting platform. A Plexiglas plate (area: $12 \times 12$ $cm^2$, height: 1.5 cm) welded to a Plexiglas cylinder (height: 13.5 cm) is then placed on the balance. A P 0 glass frit 7 cm in diameter and 0.45 cm high has been liquidtightly embedded in the Plexiglas plate, i.e., the fluid exits through the pores of the frit and not via the edge between Plexiglas plate and frit. A curved Plexiglas tube leads through the outer shell of the Plexiglas cylinder into the center of the Plexiglas cylinder to ensure fluid transportation. This tube has the same diameter as the outflow from the dropping funnel.

The fluid tube is then connected with a flexible hose (37 cm in length, 1.0 cm in external diameter, 0.7 cm in internal diameter) to the dropping funnel such that the connection does not exert any pressure on the balance.

The lifting platform is then used to adjust the upper side of the frit to the level of the bottom end of the glass tube, so that an always atmospheric flux of fluid from the dropping funnel to the measuring apparatus is ensured during measurement. The upper side of the frit is adjusted such that its surface is moist but there is no standing film of water on the frit. (Care must also be taken to ensure that there is no standing fluid in the glass tube during adjustment. If there is fluid in the glass tube, the frit has been wrongly adjusted. Furthermore, when the tap of the dropping funnel is open no uninterrupted film of fluid may form on the frit even 5 minutes after completion of the adjustment, nor may the weight of the balance change during this period. If gas bubbles are visible on the underside of the frit, they are removed, for example by employing an aspirator). During adjustment, the tap of the dropping funnel is open; as soon as the adjustment procedure is concluded, it is closed.

Satisfactory functioning is verified before every run. The fluid in the dropping funnel is made up to 1,000 ml before every run.

The dry Plexiglas cylinder has 70.0±0.1 g of water-absorbing polymeric particles weighed into it and the surface of the water-absorbing polymeric particles is smoothed. The fill level is about 3 cm. The Plexiglas cylinder is placed on the (moist) frit and the balance is tared. The tap of the dropping funnel is then opened and the measurement started.

Owing to the high loading weight the tension of the wire mesh may decrease over time (after many measurements) and the mesh may bulge out during measurement. In this case, the Plexiglas cylinder with the polymer will deviate from the vertical during measurement. There is then no longer any optimum contact between wire mesh and glass frit and consequently the imbibition of fluid decreases. In this case it is necessary to replace the wire mesh.

Procedure:

Once the apparatus is fully assembled, the tap of the dropping funnel is opened and the electronic data recording started. An increase in the weight on the balance is registered as a function of time. This then indicates how much salt solution has been imbibed by the swelling gel column of water-absorbing polymeric particles at a certain time. The gel column is allowed to swell for 60 and 240 minutes. The data are automatically captured every 10 seconds. The test can be carried out pressurelessly, without any weight on the gel column during swelling. Selectively, however, for better differentiation, it is also possible to carry out swelling under pressure, in which case the weights identified above under Absorbency under Load (AUL) can be inserted into the apparatus. Customary loadings are 0.3 psi (2.07 kPa) and 0.7 psi (4.83 kPa). The measurement is preferably carried out pressurelessly and also at 0.3 psi and 0.7 psi for a period of in each case 60 or 240 minutes per sample. The absorption data are based on the total amount of salt solution imbibed by each 70 g sample.

The amount of salt solution (in grams) imbibed altogether by the 70 g sample within a certain period is known as wicking absorption and is characterized as follows: $DA_{nn}$, where the subscripted index nn characterizes the absorption time in minutes in that, for example, $DA_{60}$ denotes pressureless absorption after 60 minutes. When pressure is employed during the swelling process, it is indicated in brackets in that, for example, $DA_{240}$ (0.3 psi) denotes absorbency under a load of 0.3 psi after 240 minutes.

Transportation Value (TV)

The product of wicking absorption and Saline Flow Conductivity (SFC) characterizes the ability of water-absorbing polymeric particles to transport fluids in the course of swelling or through the swollen layer of gel. This product of SFC and $DA_{60}$ (pressureless wicking absorption after 60 min) is designated the Transportation Value (TV) and calculated as follows:

$$TV[cm^3 s] = SFC[cm^3 s/g] \times DA_{60}[g] \times 10^7$$

Odor Test

To assess the odor of the swollen water-absorbing polymeric particles, 2.0 g of dry polymeric particles are weighed into a 50 ml glass beaker. 20 g of 0.9% by weight sodium chloride solution at 23° C. are then added. The glass beaker holding the swelling water-absorbing polymeric particles is covered with Parafilm and left to stand for 3 minutes. Thereafter, the film is removed and the odor can be assessed. Each sample is examined by at least 3 judges, a separate sample being prepared for each.

CIE Color Number (L A B)

Color measurement was carried out in accordance with the CIELAB procedure (Hunterlab, volume 8, 1996, issue 7, pages 1 to 4). In the CIELAB system, the colors are described via the coordinates L*, a* and b* of a three-dimensional system. L* indicates lightness, with L*=0 denoting black and L*=100 denoting white. The a* and b* values indicate the position of the color on the color axes red/green and yellow/blue respectively, where +a* represents red, −a* represents green, +b* represents yellow and −b* represents blue.

The color measurement complies with the three-range method of German standard specification DIN 5033-6.

The Hunter 60 value is a measure of the whiteness of surfaces and is defined as L*−3b*, i.e., the lower the value, the darker and the yellower the color is.

A Hunterlab LS 5100 colorimeter was used.

The EDANA test methods are obtainable for example at European Disposables and Nonwovens Association, Avenue Eugène Plasky 157, B-1030 Brussels, Belgium.

EXAMPLES

Example 1

Preparation of Base Polymer

A Lödige VT 5R-MK plowshare kneader 5 l in capacity was charged with 294 g of deionized water, 306.6 g of acrylic acid, 1993.0 g of 37.3% by weight sodium acrylate solution (100 mol % neutralized) and also 3.50 g of 18 tuply ethoxylated trimethylolpropane triacrylate crosslinker. This initial charge was inertized by bubbling nitrogen through it for 20 minutes. This was followed by the addition of dilute aqueous solutions of 2.453 g of sodium persulfate (dissolved in 13.9 g of water), 0.053 g of ascorbic acid (dissolved in 10.46 g of water) and also 0.146 g of 30% by weight hydrogen peroxide (dissolved in 1.31 g of water) to initiate the polymerization at about 20° C. After initiation, the temperature of the heating jacket was closed loop controlled to the reaction temperature in the reactor. The crumbly gel ultimately obtained was then dried in a circulating air drying cabinet at 160° C. for about 3 hours.

The dried base polymer was ground and classified to 300-600 μm by sieving off over- and undersize.

The properties of the polymer (300 to 600 μm) were as follows:

CRC=32 g/g

AUL 0.3 psi=26 g/g 16 h extractables=9.8% by weight pH=5.8

Example 2a 20 g of the polymer of Example 1 were introduced as an initial charge into a Waring laboratory mixer equipped with an attachment having blunt mixing blades. At a moderate number of revolutions per minute, a syringe was then used to slowly inject (through a hole in the lid of the mixing attachment) exactly 1.00 g of the postcrosslinking solution with stirring in order that the polymer may be wetted as uniformly as possible.

The postcrosslinking solution had the following composition: 0.02 g of 2-oxazolidone, 0.01 g of sorbitan monococoate, 0.97 g of water.

The moistened polymer was homogenized by stirring and then heat treated on a watchglass in a circulating air drying cabinet at 175° C. for 90 minutes. It was finally sieved through a 600 μm sieve to remove lumps.

The polymer had the following properties:

CRC=26 g/g

AUL 0.7 psi=23 g/g

SFC=129×$10^{-7}$ $cm^3$ s $g^{-1}$

FSR=0.16 g $g^{-1}$ $s^{-1}$

Example 2b 20 g of the polymer of Example 1 were introduced as an initial charge into a Waring laboratory mixer equipped with an attachment having blunt mixing blades. At a moderate number of revolutions per minute, a syringe was then used to slowly inject (through a hole in the lid of the mixing attachment) exactly 1.00 g of the postcrosslinking solution with stirring in order that the polymer may be wetted as uniformly as possible.

The postcrosslinking solution had the following composition: 0.020 g of N-hydroxyethyl-2-oxazolidone, 0.005 g of sorbitan monococoate, 0.975 g of water.

The moistened polymer was homogenized by stirring and then heat treated on a watchglass in a circulating air drying cabinet at 175° C. for 90 minutes. It was finally sieved through a 600 μm sieve to remove lumps.

The polymer had the following properties:
CRC=26.1 g/9
AUL 0.7 psi=23.5 g/g
SFC=120×10$^{-7}$ cm$^3$ s g$^{-1}$
FSR=0.16 g g$^{-1}$ s$^{-1}$ Example 2c 20 g of the polymer of Example 1 were introduced as an initial charge into a Waring laboratory mixer equipped with an attachment having blunt mixing blades. At a moderate number of revolutions per minute, a syringe was then used to slowly inject (through a hole in the lid of the mixing attachment) exactly 1.00 g of the postcrosslinking solution with stirring in order that the polymer may be wetted as uniformly as possible.

The postcrosslinking solution had the following composition: 0.020 g of 2-oxazolidone, 0.020 g of 1,2-propanediol, 0.010 g of sorbitan monococoate, 0.95 g of water.

The moistened polymer was homogenized by stirring and then heat treated on a watchglass in a circulating air drying cabinet at 175° C. for 90 minutes. It was finally sieved through a 600 μm sieve to remove lumps.

The polymer had the following properties:
CRC=25.8 g/g
AUL 0.7 psi=22.8 g/g
SFC=140×10$^{-7}$ cm$^3$ s g$^{-1}$
FSR=0.14 g g$^{-1}$ s$^{-1}$ Example 2d 20 g of the polymer of Example 1 were introduced as an initial charge into a Waring laboratory mixer equipped with an attachment having blunt mixing blades. At a moderate number of revolutions per minute, a syringe was then used to slowly inject (through a hole in the lid of the mixing attachment) exactly 1.00 g of the postcrosslinking solution with stirring in order that the polymer may be wetted as uniformly as possible.

The postcrosslinking solution had the following composition: 0.020 g of 2-oxazolidone, 0.29 g of isopropanol, 0.69 g of water.

The moistened polymer was homogenized by stirring and then heat treated on a watchglass in a circulating air drying cabinet at 175° C. for 90 minutes. It was finally sieved through a 600 μm sieve to remove lumps.

The polymer had the following properties:
CRC=25.2 g/g
AUL 0.7 psi=23.2 g/g
SFC=119×10$^{-7}$ cm$^3$ s g$^{-1}$
FSR=0.14 g g$^{-1}$ s$^{-1}$ Example 3

Preparation of Base Polymers of Different Degree of Neutralization and Postcrosslinking with 2-Oxazolidone Water-absorbing polymers were prepared similarly to Example 1 in a Lödige VT 5R-MK plowshare kneader 5 l in capacity at a solids content of 35.5% by weight and degrees of neutralization of 60 mol %, 65 mol %, 70 mol %, 75 mol % and 85 mol % and using 0.70% by weight of polyethylene glycol 400-diacrylate crosslinker (based on acrylic acid). Initiation was effected similarly to Example 1 following introduction of the initial charge of starting materials. The initial charge was inertized by bubbling nitrogen through it for 20 minutes. This was followed by the addition of dilute aqueous solutions of 2.453 g of sodium persulfate (dissolved in 13.9 g of water), 0.053 g of ascorbic acid (dissolved in 10.46 g of water) and also 0.146 g of 30% by weight hydrogen peroxide (dissolved in 1.31 g of water) to initiate the polymerization at about 20° C. After initiation, the temperature of the heating jacket was closed loop controlled to the reaction temperature in the reactor. The crumbly gel ultimately obtained was then dried in a circulating air drying cabinet at 160° C. for about 3 hours.

The dried base polymer was ground and classified to 200-850 μm by sieving off over- and undersize.

20 g of each of these polymers were introduced as an initial charge into a Waring laboratory mixer equipped with an attachment having blunt mixing blades. At a moderate number of revolutions per minute, a syringe was then used to slowly inject (through a hole in the lid of the mixing attachment) exactly 1.00 g of the postcrosslinking solution with stirring in order that the polymer may be wetted as uniformly as possible.

The composition of the postcrosslinking solution is defined such that, based on the base polymer used, 3.43% by weight of water, 1.47% by weight of isopropanol and 0.10% by weight of oxazolidone were applied. The moistened polymer was homogenized by stirring and then the polymers were heat treated on watchglasses in circulating air drying cabinets at 175° C. for 60 minutes. They were finally sieved through a 850 μm sieve to remove lumps.

The properties of the polymers thus prepared are summarized in the following table:

TABLE 1

Dependence of CRC, AUL and SFC on degree of neutralization

| Degree of neutralization | pH of polymer | CRC [g/g] | AUL 0.7 psi [g/g] | SFC [×10$^{-7}$ cm$^3$ s g$^{-1}$] |
|---|---|---|---|---|
| 85 mol % | 6.32 | 29.1 | 25.0 | 22 |
| 75 mol % | 5.97 | 29.2 | 26.8 | 45 |
| 70 mol % | 5.79 | 29.0 | 26.8 | 57 |
| 65 mol % | 5.65 | 27.5 | 26.5 | 70 |
| 60 mol % | 5.49 | 25.5 | 25.0 | 80 |

It is clear from the data that Saline Flow Conductivity (SFC) drops off sharply when the degree of neutralization is too high, but Centrifuge Retention Capacity (CRC) is strongly impaired when the degree of neutralization is too low.

Examples 5 to 14

The preparation example for the base polymer of Example 1 was repeated. The dried base polymer was ground and classified to 300-600 μm by sieving off over- and undersize. The properties of the base polymer (300 to 600 μm) were as follows:
CRC=32 g/g
AUL 0.3 psi=24 g/g
16 h extractables=8.2% by weight
pH=5.7

Postcrosslinking was carried out completely analogously to Examples 2a to 2d. The table which follows reports the starting material amounts in % by weight based on base polymer used and also the reaction conditions. Postcrosslinker 1 and if appropriate postcrosslinker 2 were dissolved together with 0.02% by weight of sorbitan monococoates (deagglomeration agent, Emulsogen V 4345 from Clariant, Germany), based on polymer used, and if appropriate the cosolvent and sprayed onto the base polymer in the Waring blender. This was followed by drying on a watchglass in a circulating air oven at the reported residence time and reaction temperature. The results are summarized in Table 2.

Example 15

Preparation of Base Polymer

The preparation example for the base polymer of Example 1 was repeated. The dried base polymer was ground and classified to 300-600 μm by sieving off over- and undersize. The properties of the base polymer (300 to 600 μm) were as follows:
CRC=33 g/g
AUL 0.3 psi=23 g/g
16 h extractables=7.8% by weight
pH=5.7

Example 16 to 36

Surface Postcrosslinking

Postcrosslinking was carried out completely analogously to Examples 2a to 2d. The table which follows reports the use levels of crosslinker in the mixture with water in % by weight based on base polymer used. For postcrosslinking, 20 g of base polymer of Example 15 at a time were sprayed, and mixed, in the Waring blender with the reported mixture which additionally comprised 0.02% by weight of sorbitan mono-

TABLE 2

Postcrosslinking of base polymer with 65 mol % degree of neutralization

| Ex. | Postcrosslinker 1 | Postcrosslinker 2 | Water | Cosolvent | Sorbitan mono-cocoate | Residence time | Reaction temperature | CRC [g/g] | AUL 0.7 psi [g/g] | SFC [×10$^{-7}$ cm$^3$ sg$^{-1}$] | Odor test |
|---|---|---|---|---|---|---|---|---|---|---|---|
| 5 | 0.10% by weight of ethylene glycol diglycidyl ether | —/— | 3.88% by weight | —/— | 0.02% by weight | 60 min | 175° C. | 27.5 | 24.4 | 91 | |
| 6 | 0.12% by weight of 2-oxazolidinone | —/— | 3.86% by weight | —/— | 0.02% by weight | 60 min | 175° C. | 26.3 | 23.0 | 121 | |
| 7 | 0.12% by weight of 2-oxazolidinone | 0.12% by weight of 1,2-propanediol | 3.74% by weight | —/— | 0.02% by weight | 60 min | 175° C. | 27.2 | 23.5 | 207 | alcoholic |
| 8 | 0.12% by weight of ethylene carbonate | —/— | 3.86% by weight | —/— | 0.02% by weight | 60 min | 175° C. | 27.0 | 23.8 | 129 | |
| 9 | 0.12% by weight of N-hydroxyethyl-2-oxazolidinone | —/— | 3.86% by weight | —/— | 0.02% by weight | 60 min | 195° C. | 25.2 | 22.1 | 117 | |
| 10 | 0.12% by weight of N-hydroxyethyl-2-oxazolidinone | 0.12% by weight of 1,2-propanediol | 3.74% by weight | —/— | 0.02% by weight | 90 min | 175° C. | 26.6 | 23.5 | 128 | alcoholic |
| 11 | 0.60% by weight of 1,2-propanediol | —/— | 3.38% by weight | —/— | 0.02% by weight | 60 min | 175° C. | 26.8 | 23.3 | 133 | alcoholic |
| 12 | 0.60% by weight of 1,2-propanediol | —/— | 2.38% by weight | 1.02% by weight isopropanol | 0.02% by weight | 60 min | 175° C. | 25.9 | 22.1 | 155 | alcoholic |
| 13 | 0.24% by weight of 5-methyl-1-aza-4,6-dioxa-bicyclo[3.3.0]octane | —/— | 3.74% by weight | —/— | 0.02% by weight | 60 min | 175° C. | 26.5 | 21.1 | 90 | |
| 14 | 0.24% by weight of 1-aza-4,6-dioxa-bicyclo[3.3.0]octane | —/— | 3.74% by weight | —/— | 0.02% by weight | 60 min | 175° C. | 26.6 | 21.8 | 92 | | cocoates (deagglomeration agent Emulsogen V 4345, Clariant, Germany) based on polymer used. This was followed by drying on a watchglass in a circulating air oven at 175° C. for 60 minutes. The results are summarized in Tables 3 and 4.

TABLE 3

Postcrosslinking with various postcrosslinkers

| Example | Postcrosslinker | Formula | Post-crosslinker % by weight | Water % by weight | CRC (g/g) | AUL 0.7 psi (g/g) | SFC ($\times 10^{-7}$) cm$^3$xs/g | CIE color no. L | a | b | Odor test |
|---|---|---|---|---|---|---|---|---|---|---|---|
| 16 | 1,2-Ethanediol | $HO(CH_2)_2OH$ | 1.32 | 2.68 | 24.5 | 21.4 | 175 | 90.1 | −0.7 | 5.7 | alcoholic |
| 17 | 1,2-Propanediol | $CH_3CH(OH)CH_2OH$ | 1.32 | 2.68 | 25.0 | 21.2 | 186 | 90.1 | −0.7 | 5.6 | alcoholic |
| 18 | 1,4-Butanediol | $HO(CH_2)_4OH$ | 1.32 | 2.68 | 26.2 | 21.4 | 189 | 90.4 | −0.7 | 5.2 | odorless |
| 19 | Trimethylolpropane ethoxylate Polyol TP 70 (n = 7) | $C_2H_5C[CH_2(OCH_2CH_2)_nOH]_3$ | 1.32 | 2.68 | 30.6 | 19.5 | 1 | 89.4 | −0.7 | 5.5 | odorless |
| 20 | Trimethylolpropane propoxylate Polyol TS 30 (n = 3) | $C_2H_5C[CH_2(OC_3H_8)_nOH]_3$ | 1.32 | 2.68 | 31.4 | 13.0 | 0 | 89.8 | −0.7 | 5.3 | odorless |
| 21 | 5-Ethyl-1,3-dioxane-5-methanol | | 1.32 | 2.68 | 31.1 | 18.4 | 4 | 90.4 | −0.7 | 5.2 | odorless |
| 22 | Di (trimethylolpropane) | $O[CH_2C(C_2H_5)(CH_2OH)_2]_2$ | 1.32 | 2.68 | 30.2 | 21.1 | 8 | 90.5 | −0.7 | 5.7 | almost odorless |
| 23 | 2,5-Hexanediol | $CH_3CH(OH)CH_2CH_2CH(OH)CH_3$ | 1.32 | 2.68 | 30.3 | 21.4 | 9 | 90.4 | −0.7 | 5.3 | reeks of aromatics |
| 24 | 2-Methyl-2,4-pentanediol | $CH_3CH(OH)CH_2C(CH_3)_2OH$ | 1.32 | 2.68 | 30.8 | 16.7 | 0 | 90.7 | −0.7 | 5.4 | reeks of aromatics |
| 25 | 2,4-Dimethyl-2,4-pentanediol | $HOC(CH_3)_2CH_2C(CH_3)_2OH$ | 1.32 | 2.68 | 30.7 | 14.2 | 0 | 90.5 | −0.7 | 5.4 | almost odorless |
| 26 | Neopentyl glycol propoxylate Polyol NS 20 (n = 2) | $(CH_3)_2C[CH_2]OCH_2CH(CH_3)]_nOH]_2$ | 1.32 | 2.68 | 30.3 | 16.8 | 3 | 90.3 | −0.7 | 5.3 | slightly fruity |
| 27 | Trimethylolpropane ethoxylate Polyol TP 30 (n = 3) | $C_2H_5C[CH_2(OCH_2CH_2)_nOH]_3$ | 1.32 | 2.68 | 29.4 | 24.2 | 28 | 90.3 | −0.7 | 5.4 | slightly alcoholic |

TABLE 4

Postcrosslinking with various preferred postcrosslinkers

| Example | Postcrosslinker | Formula | Post-crosslinker % by weight | Water % by weight | CRC (g/g) | AUL 0.7 psi (g/g) | SFC ($\times 10^{-7}$) cm$^3$xs/g | CIE color no. L | a | b | Odor test |
|---|---|---|---|---|---|---|---|---|---|---|---|
| 28 | 1,3-Propanediol | $HO(CH_2)_3OH$ | 1.32 | 2.68 | 24.6 | 21.4 | 168 | 90.8 | −0.7 | 5.2 | odorless |
| 29 | 1,5-Pentanediol | $HO(CH_2)_5OH$ | 1.32 | 2.68 | 26.9 | 21.3 | 165 | 90.4 | −0.7 | 5.2 | odorless |
| 30 | 1,6-Hexanediol | $HO(CH_2)_6OH$ | 1.32 | 2.68 | 27.6 | 23.3 | 106 | 90.5 | −0.7 | 5.3 | odorless |
| 31 | 1,7-Heptanediol | $HO(CH_2)_7OH$ | 1.32 | 2.68 | 29.4 | 23.3 | 52 | 90.5 | −0.7 | 5.3 | odorless |
| 34 | 2-Methyl-1,3-propanediol | $HOCH_2CH(CH_3)CH_2OH$ | 1.32 | 2.68 | 26.7 | 22.4 | 182 | 90.6 | −0.7 | 5.2 | odorless |
| 32 | 2,2-Dimethyl-1,3-propanediol | $HOCH_2C(CH_3)_2CH_2OH$ | 1.32 | 2.68 | 27.8 | 23.8 | 89 | 90.6 | −0.7 | 5.2 | slightly fruity |
| 33 | Trimethylolpropane ethoxylate Polyol TP 08 (n = 0.8) | $C_2H_5C[CH_2(OCH_2CH_2)_nOH]_3$ | 1.32 | 2.68 | 27.8 | 22.4 | 93 | 90.5 | −0.7 | 5.2 | odorless |
| 35 | 3-Ethyl-3-oxetanemethanol | | 1.32 | 2.68 | 27.7 | 22.4 | 131 | 90.1 | −0.6 | 5.2 | odorless |
| 36 | 1,1,1-Tris(hydroxymethyl)propane | $C_2H_5C(CH_2OH)_3$ | 1.32 | 2.68 | 27.4 | 22.1 | 111 | 90.7 | −0.7 | 5.2 | odorless |

Although good postcrosslinking results were obtained in Examples 16 to 18, when the waterabsorbing polymeric particles produced came into contact with water they either released unpleasant odors from byproducts formed or, in the case of 1,4-butanediol postcrosslinker, undesirable volatile substantially nonodorous byproducts (tetrahydrofuran) through cyclization.

In Examples 23 and 24, strong smelling byproducts were formed during postcrosslinking which were released when the waterabsorbing polymeric particles swelled in aqueous solution and which preclude the use of such polymeric particles in hygiene articles.

Examples 19 to 22 and also 25 to 27 are examples of less reactive postcrosslinkers which are preferably used as a cosolvent.

Examples 37 to 57

Surface Postcrosslinking with Reactive Crosslinker

Postcrosslinking was carried out completely analogously to Examples 2a to 2d. The table which follows reports the use levels of crosslinker in admixture with water in % by weight based on base polymer used. For postcrosslinking, 20 g of base polymer of Example 15 at a time were sprayed, and mixed, in the Waring blender with the mixture reported in the table, of crosslinker or cosolvent and 2-oxazolidone that further comprised sorbitan monococoates (deagglomeration agent Emulsogen V 4345, Clariant, Germany) in an amount of 0.02% by weight, based on polymer used. This was followed by drying on a watchglass in a circulating air oven at 175° C. for 60 minutes. The results are summarized in Tables 5 and 6.

TABLE 5

Postcrosslinking with various less reactive postcrosslinkers as a cosolvent

| Ex. | Post-crosslinker or cosolvent | Formula | Post-crosslinker % by weight | Water % by wt. | 2-Oxazolidone % by weight | CRC (g/g) | AUL 0.7 psi (g/g) | SFC ($\times 10^{-7}$ cm$^3 \times$ s/g) | CIE color no. L | a | b | Odor test |
|---|---|---|---|---|---|---|---|---|---|---|---|---|
| 37 | 1,2-Ethanediol | HO(CH$_2$)$_2$OH | 1.34 | 2.67 | 0.10 | 24.6 | 21.4 | 173 | 90.2 | −0.8 | 6.5 | alcoholic |
| 38 | 1,2-Propanediol | CH$_3$CH(OH)CH$_2$OH | 1.34 | 2.67 | 0.10 | 24.6 | 21.3 | 161 | 90.2 | −0.8 | 7.2 | alcoholic |
| 39 | 1,4-Butanediol | HO(CH$_2$)$_4$OH | 1.34 | 2.67 | 0.10 | 25.9 | 21.9 | 122 | 90.4 | −0.7 | 5.4 | odorless |
| 40 | 2,5-Hexanediol | CH$_3$CH(OH)CH$_2$CH$_2$CH(OH)CH$_3$ | 1.34 | 2.67 | 0.10 | 27.7 | 23.1 | 143 | 90.5 | −0.7 | 5.5 | reeks of aromatics |
| 41 | 2-Methyl-2,4-pentanediol | CH$_3$CH(OH)CH$_2$C(CH$_3$)$_2$OH | 1.34 | 2.67 | 0.10 | 28.0 | 23.5 | 146 | 90.5 | −0.7 | 5.6 | reeks of aromatics |

TABLE 6

Postcrosslinking with various preferred less reactive postcrosslinkers as a cosolvent

| Ex. | Postcrosslinker or cosolvent | Formula | Post-crosslinker % by weight | Water % by wt. | 2-Oxazolidone % by weight | CRC (g/g) | AUL 0.7 psi (g/g) | SFC ($\times 10^{-7}$ cm$^3$ xs/g) | CIE color no. L | a | b | Odor test |
|---|---|---|---|---|---|---|---|---|---|---|---|---|
| 42 | 1,3-Propanediol | HO(CH$_2$)$_3$OH | 1.34 | 2.67 | 0.10 | 25.1 | 21.7 | 132 | 90.7 | −0.8 | 5.8 | odorless |
| 43 | 1,5-Pentanediol | HO(CH$_2$)$_5$OH | 1.34 | 2.67 | 0.10 | 26.7 | 22.0 | 177 | 90.5 | −0.7 | 5.3 | odorless |
| 44 | 1,6-Hexanediol | HO(CH$_2$)$_6$OH | 1.34 | 2.67 | 0.10 | 27.2 | 24.0 | 145 | 90.5 | −0.7 | 5.5 | odorless |
| 45 | 1,7-Heptanediol | HO(CH$_2$)$_7$OH | 1.34 | 2.67 | 0.10 | 27.4 | 22.1 | 150 | 90.8 | −0.7 | 5.4 | odorless |
| 46 | 2,4-Dimethyl-2,4-pentanediol | HOC(CH$_3$)$_2$CH$_2$C(CH$_3$)$_2$OH | 1.34 | 2.67 | 0.10 | 27.5 | 21.7 | 138 | 90.5 | −0.7 | 5.4 | almost odorless |
| 47 | 2,2-Dimethyl-1,3-propanediol | HOCH$_2$C(CH$_3$)$_2$CH$_2$OH | 1.34 | 2.67 | 0.10 | 27.3 | 22.9 | 157 | 90.9 | −0.7 | 5.3 | slightly fruity |
| 48 | Neopentyl glycol propoxylate Polyol NS 20 (n = 2) | (CH$_3$)$_2$C[CH$_2$[OCH$_2$CH(CH$_3$)]$_n$OH]$_2$ | 1.34 | 2.67 | 0.10 | 27.9 | 23.0 | 118 | 90.5 | −0.7 | 5.4 | slightly fruity |
| 49 | Trimethylolpropane ethoxylate Polyol TP 08 (n = 0.8) | C$_2$H$_5$C[CH$_2$(OCH$_2$CH$_2$)$_n$OH]$_3$ | 1.34 | 2.67 | 0.10 | 26.8 | 22.2 | 133 | 90.6 | −0.7 | 5.4 | odorless |
| 50 | Trimethylolpropane ethoxylate Polyol TP 30 (n = 3) | C$_2$H$_5$C[CH$_2$(OCH$_2$CH$_2$)$_n$OH]$_3$ | 1.34 | 2.67 | 0.10 | 27.2 | 23.6 | 83 | 89.8 | −0.7 | 5.7 | very slightly alcoholic |
| 51 | Trimethylolpropane ethoxylate Polyol TP 70 (n = 7) | C$_2$H$_5$C[CH$_2$(OCH$_2$CH$_2$)$_n$OH]$_3$ | 1.34 | 2.67 | 0.10 | 27.7 | 24.6 | 59 | 89.4 | −0.7 | 5.8 | odorless |
| 52 | Trimethylolpropane propoxylate Polyol TS 30 (n = 3) | C$_2$H$_5$C[CH$_2$(OC$_3$H$_6$)$_n$OH]$_3$ | 1.34 | 2.67 | 0.10 | 28.1 | 24.0 | 67 | 90.2 | 0.7 | 5.7 | odorless |

TABLE 6-continued

Postcrosslinking with various preferred less reactive postcrosslinkers as a cosolvent

| Ex. | Postcrosslinker or cosolvent | Formula | Post-crosslinker % by weight | Water % by wt. | 2-Oxa-zolidone % by weight | CRC (g/g) | AUL 0.7 psi (g/g) | SFC (×10$^{-7}$ cm$^3$ xs/g) | CIE color no. L | a | b | Odor test |
|---|---|---|---|---|---|---|---|---|---|---|---|---|
| 53 | 2-Methyl-1,3-propanediol | HOCH$_2$CH(CH$_3$)CH$_2$OH | 1.34 | 2.67 | 0.10 | 26.4 | 22.8 | 164 | 90.5 | −0.7 | 5.3 | odorless |
| 54 | 3-Ethyl-3-oxetanemethanol | (structure) | 1.34 | 2.67 | 0.10 | 27.2 | 22.1 | 170 | 90.3 | −0.7 | 5.1 | odorless |
| 55 | 5-Ethyl-1,3-dioxane-5-methanol | (structure) | 1.34 | 2.67 | 0.10 | 27.8 | 23.3 | 126 | 90.4 | −0.7 | 5.3 | odorless |
| 56 | Di-(trimethylolpropane) | O[CH$_2$C(C$_2$H$_5$)(CH$_2$OH)$_2$]$_2$ | 1.34 | 2.67 | 0.10 | 27.6 | 23.7 | 59 | 89.8 | −0.8 | 6.1 | odorless |
| 57 | 1,1,1-Tris(hydroxymethyl)-propane | C$_2$H$_5$C(CH$_2$OH)$_3$ | 1.34 | 2.67 | 0.10 | 26.5 | 22.2 | 185 | 90.6 | −0.7 | 5.2 | odorless |

Examples 37, 38, 40 and 41 utilized less reactive postcrosslinkers as cosolvents which form strongly smelling byproducts which militate against any use of thus produced waterabsorbing polymeric particles in hygiene articles. Moreover, the diols of Examples 37 and 38 tend to turn slightly yellow, as evident from the somewhat elevated b color number value.

The waterabsorbing polymeric particles of Example 39 do not comprise any unpleasantly smelling compounds, but a cyclic byproduct has formed (tetrahydrofuran) which is likewise undesirable in hygiene articles.

Examples 42 to 57 utilized preferred less reactive postcrosslinkers as cosolvents for reactive crosslinkers, in this case 2-oxazolidone. These mixtures lead to virtually odorless and white products.

Example 58

Base Polymer

A two-arm semicommercial kneader having an operating capacity of 2 metric tons was charged with 1326 kg of partially neutralized aqueous sodium acrylate solution having a solids content of 36% by weight. Solids content here refers to the sum total of acrylic acid and sodium acrylate in relation to total reaction solution. The degree of neutralization was 65 mol %. 0.40% by weight (based on acrylic acid monomer) of 18-tuply ethoxylated trimethylolpropane triacrylate crosslinker was added and thoroughly mixed in and subsequently the batch was inertized with nitrogen. The temperature of this solution was 19° C.

The polymerization was initiated by speedy addition of sodium persulfate (1.27 kg dissolved in 7.2 kg of water) and ascorbic acid (18.6 g dissolved in 3.7 kg of water) with stirring, and was then continued with vigorous kneading and cooling of the reactor walls for 45 minutes in such a way that the maximum temperature in the kneader stayed below 100° C. and a finely divided clump-free gel was produced.

This gel was dried on a belt dryer, subsequently ground on a roll mill and finally sieved. The polymer powder obtained had the following properties:

CRC=34.2 g/g

AUL 0.3 psi=12.3 g/g 16 h extractables=13% by weight

Residual acrylic acid monomer=240 ppm

Residual moisture content=0.5% by weight pH=5.7-5.8

| Particle size distribution | |
|---|---|
| >850 μm | 0.1% by weight |
| 600-850 μm | 26.1% by weight |
| 300-600 μm | 48.3% by weight |
| 150-300 μm | 24.9% by weight |
| 45-150 μm | 0.7% by weight |
| <45 μm | <0.1% by weight |
| 150-850 μm | 99.2% by weight |

Example 59

Base Polymer

This base polymer was prepared completely analogously to Example 58, except that the sieving was changed so as to obtain a lower fraction of fines in the product.

CRC=34.1 g/g

AUL 0.3 psi=13.9 g/g 16 h extractables=13% by weight

Residual acrylic acid monomer=240 ppm

Residual moisture content=0.5% by weight pH=5.7

| Particle size distribution | |
|---|---|
| >850 μm | 0.1% by weight |
| 600-850 μm | 29.9% by weight |
| 300-600 μm | 55.1% by weight |
| 150-300 μm | 14.6% by weight |
| 45-150 μm | 0.4% by weight |
| <45 μm | <0.1% by weight |
| 150-850 μm | 99.6% by weight |

Example 60

Base Polymer

This base polymer was prepared completely analogously to Example 58, except that the sieving was changed so as to leave but a low fraction of oversize in the product.

CRC=33.9 g/g
AUL 0.3 psi=11.6 g/g

Examples 61 to 66

A Lödige VT 5R-MK plowshare kneader 5 l in capacity was charged with 1.2 kg of base polymer from Example 60 in each case. The respective crosslinker mixture, dissolved in an isopropanol-water mixture, was then sprayed onto the base polymer by means of a two material nozzle while stirring using the isopropanol-water solvent mixture in the amounts in the table below. All amounts reported in the table are in % by weight based on initially charged base polymer. If appropriate, an additive was additionally applied that had previously been dispersed or dissolved in the postcrosslinking solution. After spraying, the product was stirred while the reactor shell was heated by means of heating fluid, a rapid rate of heating being advantageous for the product's properties. Heating was compensation controlled in such a way that the product attained its target temperature as quickly as possible and then was heat treated there under stable conditions and with stirring. At regular intervals, at the times reported in the table (from the start of the heating up period), samples were taken and their properties determined. The results are summarized in Tables 7 and 8.

TABLE 7

Results of waterabsorbing polymeric particles A (SFC, AUL and CRC)

| Ex. | Solvent for postcrosslinking [% by wt. based on polymer] | Postcrosslinker [% by wt. based on polymer] | Additive in surface postcrosslinking solution [% by wt. based on polymer] | Oil temperature in heating jacket of Lödige reactor (beginning/end) [°C.] | Product temperature [°C.] | Time [min] | SFC [$10^{-7}$ cm$^3$ sg$^{-1}$] | AUL 0.7 psi (g/g) | CRC (g/g) |
|---|---|---|---|---|---|---|---|---|---|
| 61 | 1.2% isopropanol 2.8% water | 0.1% HEONON 0.1% 1,3-propanediol | | 215-202 | 175 | 60 | 33 | 24.6 | 28.7 |
| | | | | | 175 | 70 | 48 | 24.3 | 27.8 |
| | | | | | 175 | 80 | 57 | 23.8 | 27.6 |
| 62 | 1.2% isopropanol 2.8% water | 0.1% HEONON 0.1% 1,3-propanediol | | 250-218 | 185 | 30 | 42 | 25.1 | 28.1 |
| | | | | | 185 | 45 | 88 | 23.3 | 24.9 |
| | | | | | 185 | 80 | 128 | 21.6 | 23.3 |
| 63 | 1.2% isopropanol 2.8% water | 0.1% HEONON 0.1% 1,3-propanediol | | 240-203 | 175 | 45 | 33 | 25.5 | 29.0 |
| | | | | | 175 | 60 | 57 | 25.0 | 27.0 |
| | | | | | 175 | 70 | 64 | 24.5 | 26.5 |
| | | | | | 175 | 80 | 80 | 24.1 | 26.3 |
| 64 | 1.2% isopropanol 2.8% water | 0.1% HEONON 0.1% 1,3-propanediol | 0.5% Calcium phosphate (C13-09, fr. Budenheim) | 240-204 | 175 | 45 | 60 | 25.8 | 28.8 |
| | | | | | 175 | 60 | 91 | 25.0 | 27.0 |
| | | | | | 175 | 70 | 107 | 24.3 | 26.3 |
| | | | | | 175 | 80 | 108 | 23.8 | 25.5 |
| 65 | 1.2% isopropanol 2.8% water | 01% HEONON 0.1% 1,3-propanediol | 0.25% Aluminum sulfate | 240-204 | 175 | 45 | 48 | 23.8 | 27.9 |
| | | | | | 175 | 60 | 73 | 24.2 | 27.7 |
| | | | | | 175 | 70 | 85 | 23.2 | 26.4 |
| | | | | | 175 | 80 | 94 | 22.3 | 26.3 |
| 66 | 1.2% isopropanol 2.8% water | 0.1% HEONON 0.1% 1,3-propanediol | 0.5% Calcium phosphate (C13-09, fr. Budenheim) 0.2% Boltorn H40, (fr. Perstorp) | 240-204 | 175 | 45 | 63 | 25.6 | 29.5 |
| | | | | | 175 | 60 | 116 | 25.2 | 27.9 |
| | | | | | 175 | 70 | 119 | 23.7 | 27.3 |
| | | | | | 175 | 80 | 128 | 23.8 | 26.4 |

16 h extractables=12.9% by weight
Residual acrylic acid monomer=230 ppm
Residual moisture content=0.5% by weight
pH=5.7

| Particle size distribution | |
|---|---|
| >850 μm | <0.1% by weight |
| 600-850 μm | 1.3% by weight |
| 300-600 μm | 70.4% by weight |
| 150-300 μm | 28.9% by weight |
| 45-150 μm | 0.6% by weight |
| <45 μm | <0.1% by weight |
| 150-500 μm | 98.1% by weight |

TABLE 8

Results of waterabsorbing polymeric particles A (DA$_{60}$, DA$_{240}$ and TV)

| | | Wicking effect test | | | |
|---|---|---|---|---|---|
| Example | Time [min] | 60 min DA$_{60}$ (g/70 g) | 240 min DA$_{240}$ (g/70 g) | TV SFC × DA$_{60}$ × $10^7$ | SFC × DA$_{240}$ × $10^7$ |
| 61 | 60 | | | | |
| | 70 | | | | |
| | 80 | 303 | 412 | 17389 | 23609 |

TABLE 8-continued

Results of waterabsorbing polymeric particles A ($DA_{60}$, $DA_{240}$ and TV)

| Example | Time [min] | Wicking effect test 60 min $DA_{60}$ (g/70 g) | 240 min $DA_{240}$ (g/70 g) | TV SFC × $DA_{60}$ × $10^7$ | SFC × $DA_{240}$ × $10^7$ |
|---|---|---|---|---|---|
| 62 | 30 | | | | |
|  | 45 | 354 | 507 | 31150 | 44605 |
|  | 80 | 397 | 521 | 50626 | 66454 |
| 63 | 45 | | | | |
|  | 60 | | | | |
|  | 70 | | | | |
|  | 80 | 370 | 499 | 29633 | 39884 |
| 64 | 45 | | | | |
|  | 60 | | | | |
|  | 70 | | | | |
|  | 80 | 264 | 401 | 28464 | 43257 |
| 65 | 45 | | | | |
|  | 60 | | | | |
|  | 70 | | | | |
|  | 80 | 234 | 361 | 22015 | 33952 |
| 66 | 45 | | | | |
|  | 60 | | | | |
|  | 70 | | | | |
|  | 80 | 192 | 300 | 24600 | 38540 |

Example 67 to 78

Examples 67 to 78 were carried out completely analogously to Examples 61 to 66 except that base polymers 58 and 59 were used.

TABLE 9

Results of waterabsorbing polymeric particles B and C (SFC, AUL, CRC, FSR, $DA_{60}$, $DA_{240}$ and TV)

| Ex. | Base polymer of Example | Solvent | Postcrosslinker | Temp. °C. | Time Min. | SFC ×$10^{-7}$ cm³ s g⁻¹ | AUL 0.7 psi (g/g) | CRC (g/g) | FSR (g/gs) | Wicking effect test 60 min (g/70 g) | 240 min (g/70 g) | TV SFC × $10^7$ × $DA_{60}$ |
|---|---|---|---|---|---|---|---|---|---|---|---|---|
| 67 | 58 | 1.2% isopropanol 2.8% water | 0.1% 2-oxazolidinone 0.1% 1,3-propanediol | 175 | 30 | 30 | 25.5 | 28.3 | | | | |
|  |  |  |  | 175 | 45 | 56 | 25.0 | 28.4 | 0.22 | 285 | 375 | 16048 |
|  |  |  |  | 175 | 60 | 62 | 23.9 | 27.5 | | | | |
| 68 | 58 | 1.2% isopropanol 2.8% water | 0.1% HEONON 0.1% 1,3-propanediol | 175 | 60 | 51 | 25.4 | 29.6 | 0.19 | | | |
| 69 | 58 | 1.2% isopropanol 2.8% water | 0.1% EGDGE 0.1% 1,3-propanediol | 175 | 20 | 34 | 25.4 | 28.7 | | | | |
|  |  |  |  | 175 | 30 | 42 | 25.6 | 27.8 | | | | |
|  |  |  |  | 175 | 45 | 53 | 24.9 | 28.0 | 0.18 | 295 | 395 | 15629 |
|  |  |  |  | 175 | 60 | 58 | 24.3 | 27.6 | | | | |
| 70 | 58 | 1.2% isopropanol 2.8% water | 0.1% HEONON | 175 | 70 | 27 | 25.6 | 29.7 | | | | |
|  |  |  |  | 175 | 80 | 30 | 25.7 | 29.1 | | | | |
| 71 | 58 | 1.2% isopropanol 2.8% water | 0.1% 1,3-propanediol | 175 | 70 | 26 | 25.2 | 30.0 | | | | |
|  |  |  |  | 175 | 80 | 35 | 25.0 | 29.0 | | | | |
| 72 | 58 | 1.2% isopropanol 2.8% water | 0.1% HEONON 0.1% 1,3-propanediol 0.5% SEA (C13-09) | 175 | 60 | 40 | 25.4 | 30.2 | | | | |
|  |  |  |  | 175 | 70 | 67 | 25.2 | 29.5 | | | | |
|  |  |  |  | 175 | 80 | 89 | 24.0 | 28.1 | | 171 | 327 | 15130 |
| 73 | 59 | 1.2% isopropanol 2.8% water | 0.1% HEONON 0.1% 1,3-propanediol | 175 | 45 | 48 | 26.0 | 30.0 | 0.17 | | | |
|  |  |  |  | 175 | 60 | 79 | 25.7 | 28.6 | | | | |
|  |  |  |  | 175 | 70 | 89 | 25.2 | 27.7 | | | | |
|  |  |  |  | 175 | 80 | 108 | 24.9 | 26.8 | | | | |
| 74 | 59 | 1.2% isopropanol 2.8% water | 0.1% HEONON | 175 | 60 | 30 | 24.9 | 31.2 | | | | |
|  |  |  |  | 175 | 70 | 43 | 25.0 | 30.5 | 0.16 | | | |
|  |  |  |  | 175 | 80 | 60 | 25.3 | 29.2 | | | | |
| 75 | 59 | 1.2% isopropanol 2.8% water | 0.1% 1,3-propanediol | 175 | 60 | 32 | 24.7 | 30.6 | | | | |
|  |  |  |  | 175 | 70 | 45 | 25.2 | 29.6 | 0.17 | | | |
|  |  |  |  | 175 | 80 | 64 | 25.1 | 29.0 | | | | |
| 76 | 59 | 1.2% isopropanol 2.8% water | 0.12% HEONON 0.08% 1,2-propanediol | 175 | 45 | 26 | 24.6 | 31.3 | | | | |
|  |  |  |  | 175 | 60 | 53 | 25.6 | 29.9 | 0.19 | | | |
| 77 | 59 | 1.2% isopropanol 2.8% water | 0.2% 1,3-propanediol | 175 | 60 | 41 | 26.0 | 29.6 | | | | |
|  |  |  |  | 175 | 70 | 59 | 25.7 | 28.9 | 0.16 | | | |
|  |  |  |  | 175 | 80 | 82 | 25.1 | 28.3 | | 259 | 347 | 21305 |
| 78 | 59 | 1.2% isopropanol 2.8% water | 0.1% HEONON 0.1% 1,3-propanediol 0.5% SEA (C13-09) | 175 | 45 | 36 | 25.4 | 30.5 | | | | |
|  |  |  |  | 175 | 60 | 77 | 24.8 | 28.6 | | | | |
|  |  |  |  | 175 | 80 | 89 | 23.9 | 27.3 | | 212 | 389 | 18836 |

HEONON=N-hydroxyethyl-2-oxazolidone

SEA (C13-09)=calcium phosphate type C13-09, from Budenheim

EDGE=Ethylene glycol diglycidyl ether (Denacol EX 810, from Nagase)

Examples 67 to 72 demonstrate that by the method of the present invention high values for Centrifuge Retention Capacity (CRC) and Saline Flow Conductivity (SFC) are compatible with a very high proportion of particles <300 μm (25% by weight) in the starting material and in the end product.

Examples 73 to 78 demonstrate that by the process of the present invention Centrifuge Retention Capacity (CRC) can be further increased without impairing Saline Flow Conductivity (SFC) by reducing the fraction of particles <300 μm in the starting material and in the end product to below 15% by weight.

Example 79

Noninventive Comparative Example

The properties of commercially available water-absorbing polymeric particles ASAP 510 Z® from BASF AG are as follows:

CRC=28.0 to 28.5 g/g
AUL 0.7 psi=24.0 to 24.5 g/g
FSR=0.15 g/g s
Residual moisture content <1% by weight
pH=6.1
SFC=45 to $50 \times 10^{-7}$ cm$^3$ g s$^{-1}$
TV<15000 cm$^3$s

| Particle size distribution | |
|---|---|
| <300 μm | 15% by weight |
| 300-600 μm | 55% by weight |
| >600 μm | 30% by weight |

| FIG. 1a and 1b - List of reference numerals | |
|---|---|
| 1 | Rubber bung (bored) |
| 2 | Ground stopper for filling |
| 3 | Two neck adapter |
| 4 | Glass tube for pressure equalization |
| 5 | Dropping funnel |
| 6 | Plexiglas cylinder |
| 7 | Glass frit with porosity 0 |
| 8 | Plexiglas plate with drillings |
| 9 | Plexiglas cylinder with drillings |
| 10 | Balance with computer interface |
| 11 | Flexible pressureless hose connection |
| 12 | Tap |
| 13 | Fluid delivery tube |
| P | Hydrogel sample |
| S | Salt solution |

We claim:

1. Water-absorbing polymeric particles comprising
   a) at least one interpolymerized ethylenically unsaturated acid-functional monomer, the acid groups of the at least one acid-functional monomer bearing acid groups being more than 60 and not more than 70 mol % neutralized,
   b) at least one interpolymerized crosslinker,
   c) optionally one or more interpolymerized ethylenically and/or allylically unsaturated monomer copolymerizable with a),
   d) optionally one or more water-soluble polymer grafted wholly or partly with the monomers a), b) and if present c), and
   e) at least one converted postcrosslinker,
   wherein a Centrifuge Retention Capacity (CRC) is not less than 26 g/g, an Absorbency under Load (AUL0.7psi) is not less than 23 g/g, and a Transportation Value (TV) is not less than 15,000 cm$^3$s,
   wherein the Transportation Value (TV) is the product of Saline Flow Conductivity (SFC) and wicking absorption after 60 minutes (DA$_{60}$) multiplied by 107, and
   wherein the wicking absorption after 60 minutes (DA$_{60}$) is a weight of 0.9% by weight sodium chloride solution absorbed by 70 g of the water-absorbing polymeric particles in 60 minutes, wherein the water-absorbing polymeric particles are situated, during measurement, in a circularly round vessel which has an internal diameter of 6 cm and is sealed at its lower end by a sieve base of 36 μm mesh size, and the sieve base is in atmospheric contact with 0.9% by weight sodium chloride solution.

2. The polymeric particles according to claim 1 wherein less than 2% by weight are less than 150 μm in particle size.

3. The polymeric particles according to claim 1 wherein the acid groups of the at least one acid-functional monomer are more than 63 and not more than 69 mol % neutralized.

4. The polymeric particles according to claim 1 wherein less than 2% by weight have a particle size of above 600 μm.

5. The polymeric particles according to claim 1 wherein not less than 90% by weight have a particle size in the range from 150 to 600 μm.

6. The polymeric particles according to claim 1 wherein not less than 70% by weight have a particle size in the range from 300 to 600 μm.

7. The polymeric particles according to claim 1 that have a Saline Flow Conductivity (SFC) of not less than $80 \times 10^{-7}$ cm$^3$s/g.

8. The polymeric particles according to claim 1 wherein less than 2% by weight have a particle size of above 850 μm.

9. The polymeric particles according to claim 8 wherein not less than 90% by weight have a particle size in the range from 150 to 850 μm.

10. The polymeric particles according to claim 8 wherein above 15% by weight have a particle size of less than 300 μm.

11. The polymeric particles according claim 8 that have a Centrifuge Retention Capacity (CRC) of not less than 29 g/g.

12. The polymeric particles according to claim 8 that have a Saline Flow Conductivity (SFC) of not less than $45 \times 10^{-7}$ cm$^3$s/g.

13. The polymeric particles according to claim 1 that comprise at least one water-insoluble metal phosphate.

14. The polymeric particles according to claim 13 that have a Centrifuge Retention Capacity (CRC) of not less than 30 g/g.

15. The polymeric particles according to claim 1 wherein less than 15% by weight have a particle size of less than 300 μm.

16. The polymeric particles according to any one of claim 15 that have a Centrifuge Retention Capacity (CRC) of not less than 30 g/g.

17. The polymeric particles according to claim 15 that have a Saline Flow Conductivity (SFC) of not less than $45 \times 10^{-7}$ cm$^3$s/g.

18. A process for producing water-absorbing polymeric particles by polymerization of a monomer solution comprising
   i) at least one ethylenically unsaturated acid-functional monomer, wherein acid groups of the at least one acid-functional monomer bearing acid groups being more than 60 and not more than 70 mol % neutralized,
   ii) at least one crosslinker,
   iii) optionally one or more ethylenically and/or allylically unsaturated monomer copolymerizable with i),
   iv) optionally one or more water-soluble polymer grafted wholly or partly with the monomers i), ii) and if present iii) to provide a base polymer,
   the base polymer obtained being dried, classified, aftertreated with
   v) at least one postcrosslinker,
   before being dried and thermally postcrosslinked, which comprises the thermal postcrosslinking being discontinued when the water-absorbing polymeric particles have a Centrifuge Retention Capacity (CRC) of not less than 26 g/g, an Absorbency under Load (AUL0.7 psi) of not less than 23 g/g, and a Transportation Value (TV) of not less than 15,000 cm$^3$s,
   wherein the Transportation Value (TV) is the product of Saline Flow Conductivity (SFC) and wicking absorption after 60 minutes (DA60) multiplied by $10^7$, and
   wherein the wicking absorption after 60 minutes (DA60) is the weight of 0.9% by weight sodium chloride solution absorbed by 70 g of the water-absorbing polymeric particles in 60 minutes, wherein the water-absorbing polymeric particles are situated, during measurement, in a circularly round vessel which has an internal diameter of 6 cm and is sealed at its lower end by a sieve base of 36 μm mesh size, and the sieve base is in atmospheric contact with 0.9% by weight sodium chloride solution.

19. The process according to claim 18 wherein the acid groups of the at least one acid-functional monomer in the base polymer are more than 63 and not more than 69 mol % neutralized.

20. The process according to claim 18 wherein the at least one postcrosslinker is an amide acetal, a carbamic ester, a cyclic carbonic ester, a bisoxazoline and/or a polyhydric alcohol, the polyhydric alcohol having a molecular weight of less than 100 g/mol per hydroxyl group and no vicinal, geminal, secondary or tertiary hydroxyl groups.

21. The process according to claim 18 wherein the postcrosslinking is conducted at a temperature in the range from 160 to 210° C.

22. The process according to claim 18 wherein the at least one postcrosslinker has a boiling point of not more than 160° C. or not less than 220° C.

23. The process according to claim 18 wherein the postcrosslinker is used as an aqueous solution together with at least one cosolvent, the boiling point of the cosolvent being not more than 160° C. or not less than 220° C.

24. The process according to claim 18 wherein the at least one postcrosslinker is used as an aqueous solution in the absence of a cosolvent.

25. A hygiene article comprising water-absorbing polymeric particles according to claim 1.

26. A packaging material comprising water-absorbing polymeric particles according to claim 1.

* * * * *